(12) United States Patent
Mack et al.

(10) Patent No.: US 6,682,890 B2
(45) Date of Patent: *Jan. 27, 2004

(54) METHODS OF DIAGNOSING AND DETERMINING PROGNOSIS OF COLORECTAL CANCER

(75) Inventors: David Mack, Menlo Park, CA (US); Kurt C. Gish, San Francisco, CA (US); Keith E. Wilson, Redwood City, CA (US)

(73) Assignee: Protein Design Labs, Inc., Fremont, CA (US)

(*) Notice: Subject to any disclaimer, the term of this patent is extended or adjusted under 35 U.S.C. 154(b) by 249 days.

This patent is subject to a terminal disclaimer.

(21) Appl. No.: 09/851,588

(22) Filed: May 8, 2001

(65) Prior Publication Data

US 2002/0042067 A1 Apr. 11, 2002

Related U.S. Application Data

(63) Continuation-in-part of application No. 09/642,252, filed on Aug. 17, 2000, now abandoned, and a continuation-in-part of application No. 09/656,002, filed on Sep. 6, 2000, now Pat. No. 6,455,668.

(51) Int. Cl.[7] .......................... C12Q 1/68; C12P 19/34; C07K 5/00; C07K 16/00; C07H 21/04
(52) U.S. Cl. .................. 435/6; 435/91.1; 435/91.2; 530/300; 530/387.1; 536/23.1
(58) Field of Search ............... 435/6, 91.1, 91.2; 336/23.1; 530/300, 387.1

(56) References Cited

U.S. PATENT DOCUMENTS 6,455,668 B1 * 9/2002 Mack et al. ............... 530/300

FOREIGN PATENT DOCUMENTS

| WO | 92/15602 | 9/1992 |
| WO | 97/41224 | 11/1997 |
| WO | 97/42209 | 11/1997 |
| WO | 99/04030 | 1/1999 |
| WO | WO 200196388 A2 * 12/2001 | .......... A61K/38/17 |

OTHER PUBLICATIONS

"Molecular Biology of Colorectalk Cancer," *Curr. Probl. Cancer*, 238–299 (Sep./Oct. 1997).

Liefers et al., "Micrometastases and Survival in Stage II Colorectal Cancer," *New England J. of Med.*, 339(4):223–228 (1998).

Payne et al., "Primiany Structure, Functional Expression, and Chromosomal Localization of the Bumetanide–sensitive Na–K–CL Cotransporter in Human Colon," The Journal of Biological Chemistry, 270(30): 17977–17985 (1995).

Pallela et al., "99mTc–Labeled Vasoactive Intestinal Peptide Receptor Agonist: Functional Studies," The journal of Nuclear Medicine, 40(2): 352–360 (1999).

Yamamoto et al., "Clinical application of chimeric monoclonal antibody A7–NCS conjugate," Biotherapy, 10(3): 365–367 (1996).

Kind et al., "Expression, purification and characterization of a mouse–human chimeric antibody and chimeric Fab'fragment," Biochemical Journal, 281, part 2, 317–323 (1992).

* cited by examiner

*Primary Examiner*—Kenneth R. Horlick
*Assistant Examiner*—Young Kim
(74) *Attorney, Agent, or Firm*—Albert P. Halluin; Viola T. Kung; Howrey, Simon, Arnold & White, LLP

(57) ABSTRACT

Described herein are methods that can be used for diagnosis and prognosis of colorectal cancer. Also described herein are methods that can be used to screen candidate bioactive agents for the ability to modulate colorectal cancer. Additionally, methods and molecular targets (genes and their products) for therapeutic intervention in colorectal cancer are described.

4 Claims, 8 Drawing Sheets

```
GGCACGAGGA GAACTTAAAG AAATTCAGAT ATGTGAAGTT GATTTCCATG GAAACCTCGT    60
CATCCTCTGA TGACAGTTGT GACAGCTTTG CTTCTGATAA TTTTGCAAAC ACGAGGCTGC   120
AGTCAGTTCG GGAAGGCTGT AGGACCCGCA GCCAGTGCAG GCACTCTGGA CCTCTCAGGG   180
TGGCGATGAA GTTTCCAGCG CGGAGTACCA GGGGAGCAAC CAACAAAAAA GCAGAGTCCC   240
GCCAGCCCTC AGAGAATTCT GTGACTGATT CCAACTCCGA TTCAGAAGAT GAAAGTGGAA   300
TGAATTTTTT GGAGAAAAGG GCTTTAAATA TAAAGCAAAA CAAAGCAATG CTTGCAAAAC   360
TCATGTCTGA ATTAGAAAGC TTCCCTGGCT CGTTCCGTGG AAGCATCCC CTCCCAGGCT    420
CCGACTCACA ATCAAGGAGA CCGCGAAGGC GTACATTCCC GGGTGTTGCT TCCAGGAGAA   480
ACCCTGAACG GAGAGCTCGT CCTCTTACCA GGTCAAGGTC CCGGATCCTC GGGTCCCTTG   540
ACGCTCTACC CATGGAGGAG GAGGAGGAAG AGGATAAGTA CATGTTGGTG AGAAAGAGGA   600
AGACCGTGGA TGGCTACATG AATGAAGATG ACCTGCCCAG AACCCGTCGC TNCAGATCAT   660
CCGTGACCCT TCCGCATATA ATTCGCCCAG TGGAAGAAAT ACAGAAGGAG AGGAGTTGGA   720
GAACGTCTGC AGCAATTCTC GAAGAGAAGA TTATAACCGT TCACTGGGYT CTACTTGTCA   780
TCAATGCCGT CAGAAGACTA TTGATACCAA AACAAACTGC AGAAACCCAG ACTGCTGGGG   840
CGTTCGAGGC CAGTTCTGTG GCCCCTGCCT TCGAAACCGT TATGGTGAAG AGGTCAGGGA   900
TGCTCTGCTG GATCCGAACT GGCATTGCCC GCCTTGTCGA GGAATCTGCA ACTGCAGTTT   960
CTGCCGGCAG CGAGATGGAC GGTGTGCGAC TGGGGTCCTT GTGTATTTAG CCAAATATCA  1020
TGGCTTTGGG AATGTGCATG CCTACTTGAA AAGCCTGAAA CAGGAATTTG AAATGCAAGC  1080
ATAATATCTG GAAAATTTGC TGCCTGCCTT CTACTTCTCA AATCTTTCTT GTAAAAGTTT  1140
CCAATTTTTT TCACTGAAAC CTGAGTTAAA AATCTTGATG ATCAGCCTGT TTCATAAGAA  1200
ACTCCAATCA AGTTAMTCTT AGCAGACATG TGTTTCTGGA GCATCACAGA AGGTATATTG  1260
CTAGTTACAC TTTGCCCTCC TGCAGTTTCT TCTCTGCTCC CACCCCCCAT CTCATAGCAT  1320
TCCCCCTCTA TTTTCCATTG CTCCCTCTCC CAACCCGCTT AAGTTTTCTG AATTTCTTT   1380
TTAAAWTTAC AGTTTTAAGG AAAAGCCATA TTTTATTTAC CTGGGTGTTG GAAATAGCCC  1440
CTCCATAAAA CCCTAAGCAC TTGGAAACAC AATAATAGTA TTAACCTAAC TAGATCCTAT  1500
TGAATTTCAG AGAAGAGCCT TCTAACTTGT TTACACAAAA ACGAGTATGA TTTAGCATTC  1560
ATACTAGTTG AAATTTTTAA TAGAATCAAG GCACAAAAGT CTTAAAACCA TGTGGAAAAA  1620
TTAGGTAATT ATKGCARATT GAKGGTCYCY CAATCCCAYG WATKGSGCTT ATGKTACMAR  1680
KKGKTGTCMC AGTTRAGACY TAATTTCYCC TAATTTCTTC YGSCCGAAGG KWAAGKGGKG  1740
CGTCCRGCTT ACMCGATCAT AATTCMAAGG KTGGKGGSCA ATGTAAYMCT TAATTAAAT   1800
AATKRWGGAA GAGCYATCTG GAGATTAWGA GTAAGCTGAT TTGAATTTC AGTATAAAAC   1860
TTTAGTATAA TTGTAGTTTG CAAAGKTTAT TTCAGTTCAC ATGTAAGGKA TTGCMAATAA  1920
ATTCTTGGAC AATTTTGKAT GGAAACTTGA TATTAAAAAC TAGTCTGTGG KTCTTTGCAG  1980
TTTCTTGTAA ATTTATAAAC CAGGCACAAG GTTCAAGTTT AGATTTAAG CACTTTTATA   2040
ACAATGATAA GTGCCTTTTT GGAGATGTAA CTTTTAGCAG TTTGTTAACC TGACATCTCT  2100
GCCAGTCTAG TTTCTGGGCA GGTTTCCTGT GTCAGTATTC CCCTCCTCT TTGCATTAAT   2160
CAAGGTATTT GGTAGAGGTG AATCTAAGT GTTTGTATGT CCAATTTACT TGCATATGTA   2220
AACCATTGCT GTGCCATTCA ATGTTGATG CATAATTGGA CCTTGAATCG ATAAGTGTAA   2280
ATACAGCTTT TGATCTGTAA TGCTTTTATA CAAAAGTTTA TTTTAATAAT AAAATGTTTG  2340
TTCTAAAAAA AAAAAAAAAA AAAATTGCGG CCGCAAGCTT ATTCCCWTTA GTGAGKSWTA  2400
ATTTTAGCTT GGCACTGGCC GTCGTTTTAC AACGTCGTGA CTGGGAAAAC CCTGGCGTTA  2460
CCCAACTTAA TCGCCTTGCA GCACATCCCC CTTTCGCCAG CTGGCGTAAT AGCGAAGAGG  2520
CCCGCACCGA TCGCCCTTCC AACAGTTGC GCAGCCTGAA TGGCGAATGG GACGCGCCCT   2580
GTAGCGGCGC ATTAAGCGCG GCGGGTGTGG TGGTTACGCS CAGCGTGACC GCTACACTTG  2640
CCAGCGCCCT AGCGCCCGCT CCTTTCGCTT TCTTCCTTCC TTCTCGCMCG TTCGCCGGCT  2700
TTYCCCKCAA GCTNTAAATC GGGGC
```

FIGURE 1

METSSSSDDSCDSFASDNFANTRLQSVREGCRTRSQCRHSGPLRVAMKFPARSTRGATNKKAESRQPSENSVTDS
NSDSEDESGMNFLEKRALNIKQNKAMLAKLMSELESFPGSFRGRHPLPGSDSQSRRPRRRTFPGVASRRNPERRA
RPLTRSRSRILGSLDALPMEEEEEEDKYMLVRKRKTVDGYMNEDDLPRTRRYRSSVTLPHIIRPVEEIQKERSWR
TSAAILEEKIITVHWALLVINAVRRLLIPKQTAETQTAGAFEASSVAPAFETVMVKRSGMLCWIRTGIARLVEES
ATAVSAGSEMDGVRLGSLCI.

FIGURE 2

```
CACGAGGCGGCACGAGGGGACCGCTGACCGCGCGGCTGCTCCGCTCTCCCCGCTCCAAGCGCCGATCTGGG
CACCCGCCACCAGCATGGACGCTCGCCGCGTGCCGCAGAAAGATCTCAGAGTAAAGAAGAACTTAAAGAAA
TTCAGATATGTGAAGTTGATTTCCATGGAAACCTCGTCATCCTCTGATGACAGTTGTGACAGCTTTGCTTC
TGATAATTTTGCAAACACGAGGCTGCAGTCAGTTCGGGAAGGCTGTAGGACCCGCAGCCAGTGCAGGCACT
CTGGACCTCTCAGGGTGGCGATGAAGTTTCCAGCGCGGAGTACCAGGGGAGCAACCAACAAAAAAGCAGAG
TCCCGCCAGCCCTCAGAGAATTCTGTGACTGATTCCAACTCCGATTCAGAAGATGAAAGTGGAATGAATTT
TTTGGAGAAAAGGGCTTTAAATATAAAGCAAAACAAAGCAATGCTTGCAAAACTCATGTCTGAATTAGAAA
GCTTCCCTGGCTCGTTCCGTGGAAGACATCCCCTCCCAGGCTCCGACTCACAATCAAGGAGACCGCGAAGG
CGTACATTCCCGGGTGTTGCTTCCAGGAGAAACCCTGAACGGAGAGCTCGTCCTCTTACCAGGTCAAGGTC
CCGGATCCTCGGGTCCCTTGACGCTCTACCCATGGAGGAGGAGGAGGAAGAGGATAAGTACATGTTGGTGA
GAAAGAGGAAGACCGTGGATGGCTACATGAATGAAGATGACCTGCCCAGAAGCCGTCGCTCCAGATCATCC
GTGACCCTTCCGCATATAATTCGCCCAGTGGAAGAAATTACAGAAGGAGGAGTTGGAGAACGTCTGCAGCA
ATTCTCGAAGAGAAGATATATAACCGTTCACTGGGCTCTACTTGTCATCAATGCCGTCAGAAGACTATTGA
TACCAAAACAAACTGCAGAAACCCAGACTGCTGGGGCGTTCGAGGCCAGTTCTGTGGCCCCTGCCTTCGAA
ACCGTTATGGTGAAGAGGTCAGGGATGCTCTGCTGGATCCGAACTGGCATTGCCCGCCTTGTCGAGGAATC
TGCAACTGCAGTTTCTGCCGGCAGCGAGATGGACGGTGTGCGACTGGGGTCCTTGTGTATTTAGCCAAATA
TCATGGCTTTGGGAATGTGCATGCCTACTTGAAAAGCCTGAAACAGGAATTTGAAATGCAAGCATAATATC
TGGAAAATTTGCTGCCTGCCTTCTACTTCTCAAATCTTTCTTGTAAAAGTTTCCAATTTTTTTCACTGAAA
CCTGAGTTAAAAATCTTGATGATCAGCCTGTTTCATAAGAAACTCCAATCAAGTTAATCTTAGCAGACATG
TGTTTCTGGAGCATCACAGAAGGTATATTGCTAGTTACACTTTGCCCTCCTGCAGTTTCTTCTCTGCTCCC
ACCCCCCACCTCCATGGCAACCCCCCTCCTATTCCCAAGGCTCCCTCTCCCAACCGGCCTGGTTCCGGAA
TTTCCCTTTTAAAATTACAGTTTTAAGGAAAAGCCATATTTTATTTACCTGGGTGTTGGAAATAGCCCCTC
CATAAAACCCTAAGCACTTGGAAACACAATAATAGTATTAACCTAACTAGATCCTATTGAATTTCAGAGAA
GAGCCTTCTAACTTGTTTACACAAAAACGAGTATGATTTAGCATTCATACTAGTTGAAATTTTTAATAGAA
TCAAGGCACAAAAGTCTTAAAACCATGTGGAAAAATTAGGTAATTATTGCAGATTGATGTCTCTCAATCCC
ATGTATTGCGCTTATGTTACAAGTTGTTGTCACAGTTGAGACTTAATTTCTCCTAATTTCTTCTGCCCGAA
GGTAAAGTGGTGCGTCCAGCTTACACGATCATAATTCAAAGGTTGGTGGCAATGTAATACTTAATTAAAA
TAATGATGGAAGAGCTATCTGGAGATTATGAGTAAGCTGATTTGAATTTTCAGTATAAAACTTTAGTATAA
TTGTAGTTTGCAAAGTTTATTTCAGTTCACATGTAAGGTATTGCAAATAAATTCTTGGACAATTTTGTATG
GAAACTTGATATTAAAAACTAGTCTGTGGTTCTTTGCAGTTTCTTGTAAATTTATAAACCAGGCACAAGGT
TCAAGTTTAGATTTTAAGCACTTTTATAACAATGATAAGTGCCTTTTTGGAGATGTAACTTTTAGCAGTTT
GTTAACCTGACATCTCTGCCAGTCTAGTTTCTGGGCAGGTTTCCTGTGTCAGTATTCCCCCTCCTCTTTGC
ATTAATCAAGGTATTTGGTAGAGGTGGAATCTAAGTGTTTGTATGTCCAATTTACTTGCATATGTAAACCA
TTGCTGTGCCATTCAATGTTTGATGCATAATTGGACCTTGAATCGATAAGTGTAAATACAGCTTTTGATCT
GTAATGCTTTTATACAAAAGTTTATTTTAATAATAAAATGTTTGTTCTAACTTGTCTGCTTTTTTAAAAAT
AATCTTACTGTACTTAATTCTAATTTTTTCCTCATATTTAAATAAAAGGCCATTTCCACCTTTTCT
```

FIGURE 3

MDARRVPQKDLRVKKNLKKFRYVKLISMETSSSSDDSCDSFASDNFANTRLQSVREGCRTRS
QCRHSGPLRVAMKFPARSTRGATNKKAESRQPSENSVTDSNSDSEDESGMNFLEKRALNIKQ
NKAMLAKLMSELESFPGSFRGRHPLPGSDSQSRRPRRRTFPGVASRRNPERRARPLTRSRSR
ILGSLDALPMEEEEEEDKYMLVRKRKTVDGYMNEDDLPRSRRSRSSVTLPHIIRPVEEITEG
GVGERLQQFSKRRYITVHWALLVINAVRRLLIPKQTAETQTAGAFEASSVAPAFETVMVKRS
GMLCWIRTGIARLVEESATAVSAGSEMDGVRLGSLCI.

FIGURE 4

```
GAGAGGCAGCAGCTTGTTCAGCGGACAAGGATGCTGGGCGTGAGGGACCAAGGCCTGCCCTGCACTCGGG
CCTCCTCCAGCCAGTGCTGACCAGGGACTTCTGACCTGCTGGCCAGCCAGGACCTGTGTGGGGAGGCCCT
CCTGCTGCCTTGGGGTGACAATCTCAGCTCCAGGCTACAGGGAGACCGGGAGGATCACAGAGCCAGCATG
GTACAGGATCCTGACAGTGATCAACCTCTGAACAGCCTCGATGTCAAACCCCTGCGCAAACCCCGTATCC
CCATGGAGACCTTCAGAAAGTGTGGGGATCCCCATCATCATAGCACTACTGAGCCTGGCGAGTATCATCA
TTGTGGTTGTCCTCATCAAGGTGATTCTGGATAAATACTACTTCCTCTGCGGGCAGCCTCTCCACTTCAT
CCCGAGGAAGCAGCTGTGTGACGGAGAGCTGGACTGTCCCTTGGGGAGGACGAGGAGCACTGTGTCAAG
AGCTTCCCCGAAGGGCCTGCAGTGGCAGTCCGCCTCTCCAAGGACCGATCCACACTGCAGGTGCTGGACT
CGGCCACAGGGAACTGGTTCTCTGCCTGTTTCGACAACTTCACAGAAGCTCTCGCTGAGACAGCCTGTAG
GCAGATGGGCTACAGCAGCAAACCCACTTTCAGAGCTGTGGAGATTGGCCCAGACCAGGATCTGGATGTT
GTTGAAATCACAGAAAACAGCCAGGAGCTTCGCATGCGGAACTCAAGTGGGCCCTGTCTCTCAGGCTCCC
TGGTCTCCCTGCACTGTCTTGCCTGTGGGAAGAGCCTGAAGACCCCCGTGTGGTGGGTGGGGAGGAGGC
CTCTGTGGATTCTTGGCCTTGGCAGGTCAGCATCCAGTACGACAAACAGCACGTCTGTGGAGGGAGCATC
CTGGACCCCCACTGGGTCCTCACGGCAGCCCACTGCTTCAGGAAACATACCGATGTGTTCAACTGGAAGG
TGCGGGCAGGCTCAGACAAACTGGGCAGCTTCCCATCCCTGGCTGTGGCCAAGATCATCATCATTGAATT
CAACCCCATGTACCCCAAAGACAATGACATCGCCCTCATGAAGCTGCAGTTCCCACTCACTTTCTCAGGC
ACAGTCAGGCCCATCTGTCTGCCCTTCTTTGATGAGGAGCTCACTCCAGCCACCCCACTCTGGATCATTG
GATGGGGCTTTACGAAGCAGAATGGAGGGAAGATGTCTGACATACTGCTGCAGGCGTCAGTCCAGGTCAT
TGACAGCACACGGTGCAATGCAGACGATGCGTACCAGGGGGAAGTCACCGAGAAGATGATGTGTGCAGGC
ATCCCGGAAGGGGGTGTGGACACCTGCCAGGGTGACAGTGGTGGGCCCCTGATGTACCAATCTGACCAGT
GGCATGTGGTGGGCATCGTTAGCTGGGGCTATGGCTGCGGGGCCCGAGCACCCCAGGAGTATACACCAA
GGTCTCAGCCTATCTCAACTGGATCTACAATGTCTGGAAGGCTGAGCTGTAATGCTGCTGCCCCTTTGCA
GTGCTGGGAGCCGCTTCCTTCCTGCCCTGCCCACCTGGGGATCCCCAAAGTCAGACACAGAGCAAGAGT
CCCCTTGGGTACACCCCTCTGCCCACAGCCTCAGCATTTCTTGGAGCAGCAAAGGGCCTCAATTCCTGTA
AGAGACCCTCGCAGCCCAGAGGCGCCCAGAGGAAGTCAGCAGCCCTAGCTCGGCCACACTTGGTGCTCCC
AGCATCCCAGGGAGAGACACAGCCCACTGAACAAGGTCTCAGGGGTATTGCTAAGCCAAGAAGGAACTTT
CCCACACTACTGAATGGAAGCAGGCTGTCTTGTAAAAGCCCAGATCACTGTGGGCTGGAGAGGAGAAGGA
AAGGGTCTGCGCCAGCCCTGTCCGTCTTCACCCATCCCCAAGCCTACTAGAGCAAGAAACCAGTTGTAAT
ATAAAATGCACTGCCCTACTGTTGGTATGACTACCGTTACCTACTGTTGTCATTGTTATTACAGCTATGG
CCACTATTATTAAAGAGCTGTGTAACATCAAAAAAAAAAAAAAAAAAAA
```

FIGURE 5

VGIP▓▓▓▓▓▓▓▓▓▓▓▓▓▓▓▓▓▓▓▓▓▓▓▓▓▓▓▓▓▓▓▓CGQPLHFIPRKQLCDGELDCPLGEDEEHCV
KSFPEGPAVAVRLSKDRSTLQVLDSATGNWFSACFDNFTEALAETACRQMGYSSKPTFRAVE
IGPDQDLDVVEITENSQELRMRNSSGPCLSGSLVSLHCLACGKSLKTPRVVGGEEASVDSWP
WQVSIQYDKQHVCGGSILDPHWVLTAAHCFRKHTDVFNWKVRAGSDKLGSFPSLAVAKIII
EFNPMYPKDNDIALMKLQFPLTFSGTVRPICLPFFDEELTPATPLWIIGWGFTKQNGGKMSD
ILLQASVQVIDSTRCNADDAYQGEVTEKMMCAGIPEGGVDTCQGDSGGPLMYQSDQWHVVGI
VSWGYGCGGPSTPGVYTKVSAYLNWIYNVWKAEL.

FIGURE 6

ACACAGAGAGAGGCAGCAGCTTGCTCAGCGGACAAGGATGCTGGGCGTGAGGGACCAAGGCCTGCCCTGC
ACTCGGGCCTCCTCCAGCCAGTGCTGACCAGGGACTTCTGACCTGCTGGCCAGCCAGGACCTGTGTGGGG
AGGCCCTCCTGCTGCCTTGGGGTGACAATCTCAGCTCCAGGCTACAGGGAGACCGGGAGGATCACAGAGC
CAGCATGTTACAGGATCCTGACAGTGATCAACCTCTGAACAGCCTCGATGTCAAACCCCTGCGCAAACCC
CGTATCCCCATGGAGACCTTCAGAAAGGTGGGGATCCCCATCATCATAGCACTACTGAGCCTGGCGAGTA
TCATCATTGTGGTTGTCCTCATCAAGGTGATTCTGGATAAATACTACTTCCTCTGCGGGCAGCCTCTCCA
CTTCATCCCGAGGAAGCAGCTGTGTGACGGAGAGCTGGACTGTCCCTTGGGGGAGGACGAGGAGCACTGT
GTCAAGAGCTTCCCCGAAGGGCCTGCAGTGGCAGTCCGCCTCTCCAAGGACCGATCCACACTGCAGGTGC
TGGACTCGGCCACAGGGAACTGGTTCTCTGCCTGTTTCGACAACTTCACAGAAGCTCTCGCTGAGACAGC
CTGTAGGCAGATGGGCTACAGCAGCAAACCCACTTTCAGAGCTGTGGAGATTGGCCCAGACCAGGATCTG
GATGTTGTTGAAATCACAGAAAACAGCCAGGAGCTTCGCATGCGGAACTCAAGTGGGCCCTGTCTCTCAG
GCTCCCTGGTCTCCCTGCACTGTCTTGCCTGTGGGAAGAGCCTGAAGACCCCCGTGTGGTGGGTGGGGA
GGAGGCCTCTGTGGATTCTTGGCCTTGGCAGGTCAGCATCCAGTACGACAAACAGCACGTCTGTGGAGGG
AGCATCCTGGACCCCACTGGGTCCTCACGGCAGCCCACTGCTTCAGGAAACATACCGATGTGTTCAACT
GGAAGGTGCGGGCAGGCTCAGACAAACTGGGCAGCTTCCCATCCCTGGCTGTGGCCAAGATCATCATCAT
TGAATTCAACCCCATGTACCCCAAAGACAATGACATCGCCCTCATGAAGCTGCAGTTCCCACTCACTTTC
TCAGGCACAGTCAGGCCCATCTGTCTGCCCTTCTTTGATGAGGAGCTCACTCCAGCCACCCCACTCTGGA
TCATTGGATGGGGCTTTACGAAGCAGAATGGAGGGAAGATGTCTGACATACTGCTGCAGGCGTCAGTCCA
GGTCATTGACAGCACACGGTGCAATGCAGACGATGCGTACCAGGGGGAAGTCACCGAGAAGATGATGTGT
GCAGGCATCCCGGAAGGGGGTGTGGACACCTGCCAGGGTGACAGTGGTGGGCCCCTGATGTACCAATCTG
ACCAGTGGCATGTGGTGGGCATCGTTAGCTGGGGCTATGGCTGCGGGGCCCGAGCACCCCAGGAGTATA
CACCAAGGTCTCAGCCTATCTCAACTGGATCTACAATGTCTGGAAGGCTGAGCTGTAATGCTGCTGCCCC
TTTGCAGTGCTGGGAGCCGCTTCCTTCCTGCCCTGCCCACCTGGGGATCCCCAAAGTCAGACACAGAGC
AAGAGTCCCCTTGGGTACACCCCTCTGCCCACAGCCTCAGCATTTCTTGGAGCAGCAAAGGGCCTCAATT
CCTATAAGAGACCCTCGCAGCCCAGAGGCGCCCAGAGGAAGTCAGCAGCCCTAGCTCGGCCACACTTGGT
GCTCCCAGCATCCCAGGGAGAGACACAGCCCACTGAACAAGGTCTCAGGGGTATTGCTAAGC<u>AAGAAGG
AACTTTCCCACACTACTGAATGGAAGCAGGCTGTCTTGTAAAAGCCCAGATCACTGTGGGCTGGAGAGGA
GAAGGAAAGGGTCTGCGCCAGCCCTGTCCGTTTTCACCCATCCCCAAGCCTACTAGAGCAAGAAACCAGT
TGTAATATAAAATGCACTGCCCTACTGTTGGTATGACTACCGTTACCTACTGTTGTCATTGTTATTACAG
CTATGGCCACTATTATTAAAGAGCTGTGTAAC</u>ATTTCTGGCAAAAAAAAAA

FIGURE 7

MLQDPDSDQPLNSLDVKPLRKPRIPMETFRKVGIPIIIALLSLASIIIVVVLIKVILDKYYF
ICGQPLHFIPRKQLCDGELDCPLGEDEEHCVKSFPEGPAVAVRLSKDRSTLQVLDSATGNWF
SACFDNFTEALAETACRQMGYSSKPTFRAVEIGPDQDLDVVEITENSQELRMRNSSGPCLSG
SLVSLHCLACGKSLKTPRVVGGEEASVDSWPWQVSIQYDKQHVCGGSILDPHWVLTAAHCFR
KHTDVFNWKVRAGSDKLGSFPSLAVAKIIIEFNPMYPKDNDIALMKLQFPLTFSGTVRPIC
LPFFDEELTPATPLWIIGWGFTKQNGGKMSDILLQASVQVIDSTRCNADDAYQGEVTEKMMC
AGIPEGGVDTCQGDSGGPLMYQSDQWHVVGIVSWGYGCGGPSTPGVYTKVSAYLNWIYNVWK
AEL.

SEQUENCE LISTING

<160> NUMBER OF SEQ ID NOS: 9

<210> SEQ ID NO 1
<211> LENGTH: 2725
<212> TYPE: DNA
<213> ORGANISM: Homo sapiens
<220> FEATURE:
<221> NAME/KEY: misc_feature
<222> LOCATION: (652)..(2714)
<223> OTHER INFORMATION: "n" at postitions 652 and 2714 can be any base.

<400> SEQUENCE: 1

```
ggcacgagga gaacttaaag aaattcagat atgtgaagtt gatttccatg gaaacctcgt      60
catcctctga tgacagttgt gacagctttg cttctgataa ttttgcaaac acgaggctgc     120
agtcagttcg ggaaggctgt aggacccgca gccagtgcag gcactctgga cctctcaggg     180
tggcgatgaa gtttccagcg cggagtacca gggagcaac caacaaaaaa gcagagtccc      240
gccagccctc agagaattct gtgactgatt ccaactccga ttcagaagat gaaagtggaa     300 tgaattttt ggagaaaagg gctttaaata taaagcaaaa caaagcaatg cttgcaaaac      360
tcatgtctga attagaaagc ttccctggct cgttccgtgg aagacatccc ctcccaggct     420
ccgactcaca atcaaggaga ccgcgaaggc gtacattccc gggtgttgct tccaggagaa     480
accctgaacg gagagctcgt cctcttacca ggtcaaggtc ccggatcctc gggtcccttg     540
acgctctacc catggaggag gaggaggaag aggataagta catgttggtg agaaagagga     600
agaccgtgga tggctacatg aatgaagatg acctgcccag aacccgtcgc tncagatcat     660
```

```
ccgtgaccct tccgcatata attcgcccag tggaagaaat acagaaggag aggagttgga    720
gaacgtctgc agcaattctc gaagagaaga ttataaccgt tcactgggyt ctacttgtca    780
tcaatgccgt cagaagacta ttgataccaa acaaactgc agaaacccag actgctgggg    840
cgttcgaggc cagttctgtg gcccctgcct tcgaaaccgt tatggtgaag aggtcaggga    900
tgctctgctg gatccgaact ggcattgccc gccttgtcga ggaatctgca actgcagttt    960
ctgccggcag cgagatggac ggtgtgcgac tggggtcctt gtgtatttag ccaaatatca   1020
tggctttggg aatgtgcatg cctacttgaa aagcctgaaa caggaatttg aaatgcaagc   1080
ataatatctg gaaaatttgc tgcctgcctt ctacttctca aatctttctt gtaaaagttt   1140
ccaatttttt tcactgaaac ctgagttaaa aatcttgatg atcagcctgt ttcataagaa   1200
actccaatca agttamtctt agcagacatg tgtttctgga gcatcacaga aggtatattg   1260
ctagttacac tttgccctcc tgcagtttct tctctgctcc cacccccat ctcatagcat    1320
tccccctcta ttttccattg ctccctctcc caacccgctt aagttttctg aattttcttt   1380
ttaaawttac agttttaagg aaaagccata ttttatttac ctgggtgttg gaaatagccc   1440
ctccataaaa ccctaagcac ttggaaacac aataatagta ttaacctaac tagatcctat   1500
tgaatttcag agaagagcct tctaacttgt ttacacaaaa acgagtatga tttagcattc   1560
atactagttg aaattttaa tagaatcaag gcacaaaagt cttaaaacca tgtggaaaaa    1620
ttaggtaatt atkgcaratt gakggtcycy caatcccayg watkgsgctt atgktacmar   1680
kkgktgtcmc agttragacy taatttcycc taatttcttc ygsccgaagg kwaagkggkg   1740
cgtccrgctt acmcgatcat aattcmaagg ktggkggsca atgtaaymct taattaaaat   1800
aatkrwggaa gagcyatctg gagattawga gtaagctgat ttgaattttc agtataaaac   1860
tttagtataa ttgtagtttg caaagkttat ttcagttcac atgtaaggka ttgcmaataa   1920
attcttggac aattttgkat ggaaacttga tattaaaaac tagtctgtgg ktctttgcag   1980
tttcttgtaa atttataaac caggcacaag gttcaagttt agatttaag cactttttata   2040
acaatgataa gtgccttttt ggagatgtaa ctttagcag tttgttaacc tgacatctct    2100
gccagtctag tttctgggca ggtttcctgt gtcagtattc cccctcctct ttgcattaat   2160
caaggtattt ggtagaggtg gaatctaagt gtttgtatgt ccaatttact tgcatatgta   2220
aaccattgct gtgccattca atgtttgatg cataattgga ccttgaatcg ataagtgtaa   2280
atacagcttt tgatctgtaa tgcttttata caaaagttta ttttaataat aaaatgtttg   2340
ttctaaaaaa aaaaaaaaa aaaattgcgg ccgcaagctt attcccwtta gtgagkswta    2400
attttagctt ggcactggcc gtcgttttac aacgtcgtga ctgggaaaac cctggcgtta   2460
cccaacttaa tcgccttgca gcacatcccc ctttcgccag ctggcgtaat agcgaagagg   2520
cccgcaccga tcgcccttcc caacagttgc gcagcctgaa tggcgaatgg gacgcgccct   2580
gtagcggcgc attaagcgcg gcgggtgtgg tggttacgcs cagcgtgacc gctacacttg   2640
ccagcgccct agcgcccgct cctttcgctt tcttccttcc ttctcgcmcg ttcgccggct   2700
ttycccckcaa gctntaaatc ggggc                                        2725
```

<210> SEQ ID NO 2
<211> LENGTH: 320
<212> TYPE: PRT
<213> ORGANISM: Homo sapiens

<400> SEQUENCE: 2

```
Met Glu Thr Ser Ser Ser Asp Asp Ser Cys Asp Ser Phe Ala Ser
1               5                   10                  15

Asp Asn Phe Ala Asn Thr Arg Leu Gln Ser Val Arg Glu Gly Cys Arg
            20                  25                  30

Thr Arg Ser Gln Cys Arg His Ser Gly Pro Leu Arg Val Ala Met Lys
        35                  40                  45

Phe Pro Ala Arg Ser Thr Arg Gly Ala Thr Asn Lys Lys Ala Glu Ser
50                  55                  60

Arg Gln Pro Ser Glu Asn Ser Val Thr Asp Ser Asn Ser Asp Ser Glu
65                  70                  75                  80

Asp Glu Ser Gly Met Asn Phe Leu Glu Lys Arg Ala Leu Asn Ile Lys
                85                  90                  95

Gln Asn Lys Ala Met Leu Ala Lys Leu Met Ser Glu Leu Glu Ser Phe
            100                 105                 110

Pro Gly Ser Phe Arg Gly Arg His Pro Leu Pro Gly Ser Asp Ser Gln
            115                 120                 125

Ser Arg Arg Pro Arg Arg Arg Thr Phe Pro Gly Val Ala Ser Arg Arg
130                 135                 140

Asn Pro Glu Arg Arg Ala Arg Pro Leu Thr Arg Ser Arg Ser Arg Ile
145                 150                 155                 160

Leu Gly Ser Leu Asp Ala Leu Pro Met Glu Glu Glu Glu Glu Glu Asp
                165                 170                 175

Lys Tyr Met Leu Val Arg Lys Arg Lys Thr Val Asp Gly Tyr Met Asn
            180                 185                 190

Glu Asp Asp Leu Pro Arg Thr Arg Arg Tyr Arg Ser Val Thr Leu
195                 200                 205

Pro His Ile Ile Arg Pro Val Glu Glu Ile Gln Lys Glu Arg Ser Trp
210                 215                 220

Arg Thr Ser Ala Ala Ile Leu Glu Glu Lys Ile Ile Thr Val His Trp
225                 230                 235                 240

Ala Leu Leu Val Ile Asn Ala Val Arg Arg Leu Leu Ile Pro Lys Gln
            245                 250                 255

Thr Ala Glu Thr Gln Thr Ala Gly Ala Phe Glu Ala Ser Ser Val Ala
            260                 265                 270

Pro Ala Phe Glu Thr Val Met Val Lys Arg Ser Gly Met Leu Cys Trp
            275                 280                 285

Ile Arg Thr Gly Ile Ala Arg Leu Val Glu Glu Ser Ala Thr Ala Val
            290                 295                 300

Ser Ala Gly Ser Glu Met Asp Gly Val Arg Leu Gly Ser Leu Cys Ile
305                 310                 315                 320

<210> SEQ ID NO 3
<211> LENGTH: 2551
<212> TYPE: DNA
<213> ORGANISM: Homo sapiens
<220> FEATURE:
<221> NAME/KEY: CDS
<222> LOCATION: (86)..(1129)
<223> OTHER INFORMATION:

<400> SEQUENCE: 3
cacgaggcgg cacgagggga ccgctgaccg cgcggctgct ccgctctccc cgctccaagc    60
gccgatctgg gcacccgcca ccagc atg gac gct cgc cgc gtg ccg cag aaa   112
                            Met Asp Ala Arg Arg Val Pro Gln Lys
                              1               5 gat ctc aga gta aag aag aac tta aag aaa ttc aga tat gtg aag ttg   160
```

| | | |
|---|---|---|
| Asp Leu Arg Val Lys Lys Asn Leu Lys Lys Phe Arg Tyr Val Lys Leu<br>10                    15                      20                      25 | |
| att tcc atg gaa acc tcg tca tcc tct gat gac agt tgt gac agc ttt<br>Ile Ser Met Glu Thr Ser Ser Ser Ser Asp Asp Ser Cys Asp Ser Phe<br>                  30                      35                      40 | 208 |
| gct tct gat aat ttt gca aac acg agg ctg cag tca gtt cgg gaa ggc<br>Ala Ser Asp Asn Phe Ala Asn Thr Arg Leu Gln Ser Val Arg Glu Gly<br>            45                      50                      55 | 256 |
| tgt agg acc cgc agc cag tgc agg cac tct gga cct ctc agg gtg gcg<br>Cys Arg Thr Arg Ser Gln Cys Arg His Ser Gly Pro Leu Arg Val Ala<br>    60                      65                      70 | 304 |
| atg aag ttt cca gcg cgg agt acc agg gga gca acc aac aaa aaa gca<br>Met Lys Phe Pro Ala Arg Ser Thr Arg Gly Ala Thr Asn Lys Lys Ala<br>75                      80                      85 | 352 |
| gag tcc cgc cag ccc tca gag aat tct gtg act gat tcc aac tcc gat<br>Glu Ser Arg Gln Pro Ser Glu Asn Ser Val Thr Asp Ser Asn Ser Asp<br>90                      95                    100               105 | 400 |
| tca gaa gat gaa agt gga atg aat ttt ttg gag aaa agg gct tta aat<br>Ser Glu Asp Glu Ser Gly Met Asn Phe Leu Glu Lys Arg Ala Leu Asn<br>                  110                      115               120 | 448 |
| ata aag caa aac aaa gca atg ctt gca aaa ctc atg tct gaa tta gaa<br>Ile Lys Gln Asn Lys Ala Met Leu Ala Lys Leu Met Ser Glu Leu Glu<br>             125                     130                   135 | 496 |
| agc ttc cct ggc tcg ttc cgt gga aga cat ccc ctc cca ggc tcc gac<br>Ser Phe Pro Gly Ser Phe Arg Gly Arg His Pro Leu Pro Gly Ser Asp<br>        140                      145                      150 | 544 |
| tca caa tca agg aga ccg cga agg cgt aca ttc ccg ggt gtt gct tcc<br>Ser Gln Ser Arg Arg Pro Arg Arg Arg Thr Phe Pro Gly Val Ala Ser<br>       155                      160                      165 | 592 |
| agg aga aac cct gaa cgg aga gct cgt cct ctt acc agg tca agg tcc<br>Arg Arg Asn Pro Glu Arg Arg Ala Arg Pro Leu Thr Arg Ser Arg Ser<br>170                   175                      180               185 | 640 |
| cgg atc ctc ggg tcc ctt gac gct cta ccc atg gag gag gag gag gaa<br>Arg Ile Leu Gly Ser Leu Asp Ala Leu Pro Met Glu Glu Glu Glu Glu<br>                  190                      195               200 | 688 |
| gag gat aag tac atg ttg gtg aga aag agg aag acc gtg gat ggc tac<br>Glu Asp Lys Tyr Met Leu Val Arg Lys Arg Lys Thr Val Asp Gly Tyr<br>             205                     210                   215 | 736 |
| atg aat gaa gat gac ctg ccc aga agc cgt cgc tcc aga tca tcc gtg<br>Met Asn Glu Asp Asp Leu Pro Arg Ser Arg Arg Ser Arg Ser Ser Val<br>        220                      225                      230 | 784 |
| acc ctt ccg cat ata att cgc cca gtg gaa gaa att aca gaa gga gga<br>Thr Leu Pro His Ile Ile Arg Pro Val Glu Glu Ile Thr Glu Gly Gly<br>     235                      240                      245 | 832 |
| gtt gga gaa cgt ctg cag caa ttc tcg aag aga aga tat ata acc gtt<br>Val Gly Glu Arg Leu Gln Gln Phe Ser Lys Arg Arg Tyr Ile Thr Val<br>250                      255                      260               265 | 880 |
| cac tgg gct cta ctt gtc atc aat gcc gtc aga aga cta ttg ata cca<br>His Trp Ala Leu Leu Val Ile Asn Ala Val Arg Arg Leu Leu Ile Pro<br>                  270                      275               280 | 928 |
| aaa caa act gca gaa acc cag act gct ggg gcg ttc gag gcc agt tct<br>Lys Gln Thr Ala Glu Thr Gln Thr Ala Gly Ala Phe Glu Ala Ser Ser<br>             285                     290                   295 | 976 |
| gtg gcc cct gcc ttc gaa acc gtt atg gtg aag agg tca ggg atg ctc<br>Val Ala Pro Ala Phe Glu Thr Val Met Val Lys Arg Ser Gly Met Leu<br>        300                      305                      310 | 1024 |
| tgc tgg atc cga act ggc att gcc cgc ctt gtc gag gaa tct gca act<br>Cys Trp Ile Arg Thr Gly Ile Ala Arg Leu Val Glu Glu Ser Ala Thr<br>     315                      320                      325 | 1072 |

```
gca gtt tct gcc ggc agc gag atg gac ggt gtg cga ctg ggg tcc ttg    1120
Ala Val Ser Ala Gly Ser Glu Met Asp Gly Val Arg Leu Gly Ser Leu
330             335                 340                 345 tgt att tag ccaaatatca tggctttggg aatgtgcatg cctacttgaa             1169
Cys Ile aagcctgaaa caggaatttg aaatgcaagc ataatatctg gaaaatttgc tgcctgcctt   1229
ctacttctca aatctttctt gtaaaagttt ccaattttt  tcactgaaac ctgagttaaa   1289
aatcttgatg atcagcctgt ttcataagaa actccaatca agttaatctt agcagacatg   1349
tgtttctgga gcatcacaga aggtatattg ctagttacac tttgccctcc tgcagtttct   1409
tctctgctcc acccccccac ctccatggca acccccctcc tattcccccaa ggctccctct  1469
cccaaccggc ctggttccgg aatttcccctt taaaattac agttttaagg aaaagccata   1529
ttttatttac ctgggtgttg gaaatagccc ctccataaaa ccctaagcac ttggaaacac   1589
aataatagta ttaacctaac tagatcctat tgaatttcag agaagagcct tctaacttgt   1649
ttacacaaaa acgagtatga tttagcattc atactagttg aattttttaa tagaatcaag   1709
gcacaaaagt cttaaaacca tgtggaaaaa ttaggtaatt attgcagatt gatgtctctc   1769
aatcccatgt attgcgctta tgttacaagt tgttgtcaca gttgagactt aatttctcct   1829
aatttcttct gcccgaaggt aaagtggtgc gtccagctta cacgatcata attcaaaggt   1889
tggtgggcaa tgtaatactt aattaaaata atgatggaag agctatctgg agattatgag   1949
taagctgatt tgaattttca gtataaaact ttagtataat tgtagtttgc aaagtttatt   2009
tcagttcaca tgtaaggtat tgcaaataaa ttcttggaca attttgtatg gaaacttgat   2069
attaaaaact agtctgtggt tctttgcagt ttcttgtaaa tttataaacc aggcacaagg   2129
ttcaagttta gattttaagc acttttataa caatgataag tgccttttg  gagatgtaac   2189
ttttagcagt ttgttaacct gacatctctg ccagtctagt ttctgggcag gtttcctgtg   2249
tcagtattcc ccctcctctt tgcattaatc aaggtatttg gtagaggtgg aatctaagtg   2309
tttgtatgtc caatttactt gcatatgtaa accattgctg tgccattcaa tgtttgatgc   2369
ataattggac cttgaatcga taagtgtaaa tacagctttt gatctgtaat gcttttatac   2429
aaaagtttat tttaataata aaatgtttgt tctaacttgt ctgcttttt  aaaaataatc   2489
ttactgtact taattctaat tttttcctca tatttaaata aaaggccatt tccacctttt   2549
ct                                                                  2551
```

<210> SEQ ID NO 4
<211> LENGTH: 347
<212> TYPE: PRT
<213> ORGANISM: Homo sapiens

<400> SEQUENCE: 4

```
Met Asp Ala Arg Arg Val Pro Gln Lys Asp Leu Arg Val Lys Lys Asn
1               5                   10                  15

Leu Lys Lys Phe Arg Tyr Val Lys Leu Ile Ser Met Glu Thr Ser Ser
                20                  25                  30

Ser Ser Asp Asp Ser Cys Asp Ser Phe Ala Ser Asp Asn Phe Ala Asn
            35                  40                  45

Thr Arg Leu Gln Ser Val Arg Glu Gly Cys Arg Thr Arg Ser Gln Cys
        50                  55                  60

Arg His Ser Gly Pro Leu Arg Val Ala Met Lys Phe Pro Ala Arg Ser
65                  70                  75                  80

Thr Arg Gly Ala Thr Asn Lys Lys Ala Glu Ser Arg Gln Pro Ser Glu
```

|            |            |            |            |            |            |
|---|---|---|---|---|---|
|            | 85         |            | 90         |            | 95         |

Asn Ser Val Thr Asp Ser Asn Ser Asp Ser Glu Asp Glu Ser Gly Met
            100                 105                 110

Asn Phe Leu Glu Lys Arg Ala Leu Asn Ile Lys Gln Asn Lys Ala Met
            115                 120                 125

Leu Ala Lys Leu Met Ser Glu Leu Glu Ser Phe Pro Gly Ser Phe Arg
130                 135                 140

Gly Arg His Pro Leu Pro Gly Ser Asp Ser Gln Ser Arg Arg Pro Arg
145                 150                 155                 160

Arg Arg Thr Phe Pro Gly Val Ala Ser Arg Asn Pro Glu Arg Arg
            165                 170                 175

Ala Arg Pro Leu Thr Arg Ser Arg Ser Arg Ile Leu Gly Ser Leu Asp
            180                 185                 190

Ala Leu Pro Met Glu Glu Glu Glu Glu Asp Lys Tyr Met Leu Val
            195                 200                 205

Arg Lys Arg Lys Thr Val Asp Gly Tyr Met Asn Glu Asp Asp Leu Pro
210                 215                 220

Arg Ser Arg Arg Ser Arg Ser Val Thr Leu Pro His Ile Ile Arg
225                 230                 235                 240

Pro Val Glu Glu Ile Thr Glu Gly Gly Val Gly Glu Arg Leu Gln Gln
            245                 250                 255

Phe Ser Lys Arg Arg Tyr Ile Thr Val His Trp Ala Leu Leu Val Ile
            260                 265                 270

Asn Ala Val Arg Arg Leu Leu Ile Pro Lys Gln Thr Ala Glu Thr Gln
            275                 280                 285

Thr Ala Gly Ala Phe Glu Ala Ser Ser Val Ala Pro Ala Phe Glu Thr
            290                 295                 300

Val Met Val Lys Arg Ser Gly Met Leu Cys Trp Ile Arg Thr Gly Ile
305                 310                 315                 320

Ala Arg Leu Val Glu Glu Ser Ala Thr Ala Val Ser Ala Gly Ser Glu
            325                 330                 335

Met Asp Gly Val Arg Leu Gly Ser Leu Cys Ile
            340                 345

<210> SEQ ID NO 5
<211> LENGTH: 2079
<212> TYPE: DNA
<213> ORGANISM: Homo sapiens

<400> SEQUENCE: 5

| | | | | |
|---|---|---|---|---|
| gagaggcagc | agcttgttca | gcggacaagg | atgctgggcg | tgagggacca | aggcctgccc | 60 |
| tgcactcggg | cctcctccag | ccagtgctga | ccagggactt | ctgacctgct | ggccagccag | 120 |
| gacctgtgtg | gggaggccct | cctgctgcct | tggggtgaca | atctcagctc | caggctacag | 180 |
| ggagaccggg | aggatcacag | agccagcatg | gtacaggatc | ctgacagtga | tcaacctctg | 240 |
| aacagcctcg | atgtcaaacc | cctgcgcaaa | ccccgtatcc | ccatggagac | cttcagaaag | 300 |
| tgtggggatc | cccatcatca | tagcactact | gagcctggcg | agtatcatca | ttgtggttgt | 360 |
| cctcatcaag | gtgattctgg | ataaatacta | cttcctctgc | gggcagcctc | tccacttcat | 420 |
| cccgaggaag | cagctgtgtg | acggagagct | ggactgtccc | ttggggagg | acgaggagca | 480 |
| ctgtgtcaag | agcttccccg | aagggcctgc | agtggcagtc | cgcctctcca | aggaccgatc | 540 |
| cacactgcag | gtgctggact | cggccacagg | gaactggttc | tctgcctgtt | tcgacaactt | 600 |
| cacagaagct | ctcgctgaga | cagcctgtag | gcagatgggc | tacagcagca | aacccacttt | 660 |

-continued

```
cagagctgtg gagattggcc cagaccagga tctggatgtt gttgaaatca cagaaaacag    720
ccaggagctt cgcatgcgga actcaagtgg gccctgtctc tcaggctccc tggtctccct    780
gcactgtctt gcctgtggga agagcctgaa accccccgt gtggtgggtg gggaggaggc     840
ctctgtggat tcttggcctt ggcaggtcag catccagtac gacaaacagc acgtctgtgg    900
agggagcatc ctggaccccc actgggtcct cacggcagcc cactgcttca ggaaacatac    960
cgatgtgttc aactggaagg tgcgggcagg ctcagacaaa ctgggcagct tccatccct   1020 ggctgtggcc aagatcatca tcattgaatt caaccccatg taccccaaag acaatgacat   1080
cgccctcatg aagctgcagt tcccactcac tttctcaggc acagtcaggc ccatctgtct   1140
gcccttcttt gatgaggagc tcactccagc cacccccactc tggatcattg atggggctt   1200 tacgaagcag aatggaggga agatgtctga catactgctg caggcgtcag tccaggtcat   1260
tgacagcaca cggtgcaatg cagacgatgc gtaccagggg gaagtcaccg agaagatgat   1320
gtgtgcaggc atcccggaag ggggtgtgga cacctgccag ggtgacagtg gtgggcccct   1380
gatgtaccaa tctgaccagt ggcatgtggt gggcatcgtt agctggggct atggctgcgg   1440
gggcccgagc accccaggag tatacaccaa ggtctcagcc tatctcaact ggatctacaa   1500
tgtctggaag gctgagctgt aatgctgctg ccccttttgca gtgctgggag ccgcttcctt   1560
cctgccctgc ccacctgggg atcccccaaa gtcagacaca gagcaagagt ccccttgggt   1620
acacccctct gcccacagcc tcagcatttc ttggagcagc aaagggcctc aattcctgta   1680
agagaccctc gcagcccaga ggcgcccaga ggaagtcagc agccctagct cggccacact   1740
tggtgctccc agcatcccag ggagagacac agcccactga caaggtctc aggggtattg    1800 ctaagccaag aaggaacttt cccacactac tgaatggaag caggctgtct tgtaaaagcc   1860
cagatcactg tgggctggag aggagaagga aagggtctgc gccagccctg tccgtcttca   1920
cccatcccca agcctactag agcaagaaac cagttgtaat ataaaatgca ctgccctact   1980
gttggtatga ctaccgttac ctactgttgt cattgttatt acagctatgg ccactattat   2040
taaagagctg tgtaacatca aaaaaaaaaa aaaaaaaa                            2079
```

<210> SEQ ID NO 6
<211> LENGTH: 406
<212> TYPE: PRT
<213> ORGANISM: Homo sapiens

<400> SEQUENCE: 6

```
Val Gly Ile Pro Ile Ile Ala Leu Leu Ser Leu Ala Ser Ile Ile
1               5                   10                  15

Ile Val Val Val Leu Ile Lys Val Ile Leu Asp Lys Tyr Tyr Phe Leu
                20                  25                  30

Cys Gly Gln Pro Leu His Phe Ile Pro Arg Lys Gln Leu Cys Asp Gly
            35                  40                  45

Glu Leu Asp Cys Pro Leu Gly Glu Asp Glu His Cys Val Lys Ser
        50                  55                  60

Phe Pro Glu Gly Pro Ala Val Ala Val Arg Leu Ser Lys Asp Arg Ser
65                  70                  75                  80

Thr Leu Gln Val Leu Asp Ser Ala Thr Gly Asn Trp Phe Ser Ala Cys
                85                  90                  95

Phe Asp Asn Phe Thr Glu Ala Leu Ala Glu Thr Ala Cys Arg Gln Met
                100                 105                 110

Gly Tyr Ser Ser Lys Pro Thr Phe Arg Ala Val Glu Ile Gly Pro Asp
```

-continued

```
        115                 120                 125

Gln Asp Leu Asp Val Val Glu Ile Thr Glu Asn Ser Gln Glu Leu Arg
    130                 135                 140

Met Arg Asn Ser Ser Gly Pro Cys Leu Ser Gly Ser Leu Val Ser Leu
145                 150                 155                 160
His Cys Leu Ala Cys Gly Lys Ser Leu Lys Thr Pro Arg Val Val Gly
                165                 170                 175
Gly Glu Glu Ala Ser Val Asp Ser Trp Pro Trp Gln Val Ser Ile Gln
            180                 185                 190

Tyr Asp Lys Gln His Val Cys Gly Gly Ser Ile Leu Asp Pro His Trp
        195                 200                 205

Val Leu Thr Ala Ala His Cys Phe Arg Lys His Thr Asp Val Phe Asn
    210                 215                 220
Trp Lys Val Arg Ala Gly Ser Asp Lys Leu Gly Ser Phe Pro Ser Leu
225                 230                 235                 240

Ala Val Ala Lys Ile Ile Ile Ile Glu Phe Asn Pro Met Tyr Pro Lys
                245                 250                 255
Asp Asn Asp Ile Ala Leu Met Lys Leu Gln Phe Pro Leu Thr Phe Ser
            260                 265                 270
Gly Thr Val Arg Pro Ile Cys Leu Pro Phe Phe Asp Glu Glu Leu Thr
        275                 280                 285

Pro Ala Thr Pro Leu Trp Ile Ile Gly Trp Gly Phe Thr Lys Gln Asn
    290                 295                 300
Gly Gly Lys Met Ser Asp Ile Leu Leu Gln Ala Ser Val Gln Val Ile
305                 310                 315                 320
Asp Ser Thr Arg Cys Asn Ala Asp Asp Ala Tyr Gln Gly Glu Val Thr
                325                 330                 335
Glu Lys Met Met Cys Ala Gly Ile Pro Glu Gly Gly Val Asp Thr Cys
            340                 345                 350
Gln Gly Asp Ser Gly Gly Pro Leu Met Tyr Gln Ser Asp Gln Trp His
        355                 360                 365

Val Val Gly Ile Val Ser Trp Gly Tyr Gly Cys Gly Gly Pro Ser Thr
    370                 375                 380
Pro Gly Val Tyr Thr Lys Val Ser Ala Tyr Leu Asn Trp Ile Tyr Asn
385                 390                 395                 400
Val Trp Lys Ala Glu Leu
                405

<210> SEQ ID NO 7
<211> LENGTH: 2081
<212> TYPE: DNA
<213> ORGANISM: Homo sapiens
<220> FEATURE:
<221> NAME/KEY: CDS
<222> LOCATION: (215)..(1528)
<223> OTHER INFORMATION:

<400> SEQUENCE: 7
acacagagag aggcagcagc ttgctcagcg gacaaggatg ctgggcgtga gggaccaagg     60
cctgccctgc actcgggcct cctccagcca gtgctgacca gggacttctg acctgctggc    120
cagccaggac ctgtgtgggg aggccctcct gctgccttgg ggtgacaatc tcagctccag    180
gctacaggga gaccgggagg atcacagagc cagc atg tta cag gat cct gac agt    235
                                      Met Leu Gln Asp Pro Asp Ser
                                      1               5
```

-continued

| | |
|---|---|
| gat caa cct ctg aac agc ctc gat gtc aaa ccc ctg cgc aaa ccc cgt<br>Asp Gln Pro Leu Asn Ser Leu Asp Val Lys Pro Leu Arg Lys Pro Arg<br>10                             15                     20 | 283 |
| atc ccc atg gag acc ttc aga aag gtg ggg atc ccc atc ata gca<br>Ile Pro Met Glu Thr Phe Arg Lys Val Gly Ile Pro Ile Ile Ile Ala<br>25                           30                     35 | 331 |
| cta ctg agc ctg gcg agt atc atc att gtg gtt gtc ctc atc aag gtg<br>Leu Leu Ser Leu Ala Ser Ile Ile Ile Val Val Val Leu Ile Lys Val<br>40                        45                     50                     55 | 379 |
| att ctg gat aaa tac tac ttc ctc tgc ggg cag cct ctc cac ttc atc<br>Ile Leu Asp Lys Tyr Tyr Phe Leu Cys Gly Gln Pro Leu His Phe Ile<br>                     60                           65                     70 | 427 |
| ccg agg aag cag ctg tgt gac gga gag ctg gac tgt ccc ttg ggg gag<br>Pro Arg Lys Gln Leu Cys Asp Gly Glu Leu Asp Cys Pro Leu Gly Glu<br>        75                         80                     85 | 475 |
| gac gag gag cac tgt gtc aag agc ttc ccc gaa ggg cct gca gtg gca<br>Asp Glu Glu His Cys Val Lys Ser Phe Pro Glu Gly Pro Ala Val Ala<br>                    90                         95                    100 | 523 |
| gtc cgc ctc tcc aag gac cga tcc aca ctg cag gtg ctg gac tcg gcc<br>Val Arg Leu Ser Lys Asp Arg Ser Thr Leu Gln Val Leu Asp Ser Ala<br>105                         110                    115 | 571 |
| aca ggg aac tgg ttc tct gcc tgt ttc gac aac ttc aca gaa gct ctc<br>Thr Gly Asn Trp Phe Ser Ala Cys Phe Asp Asn Phe Thr Glu Ala Leu<br>120                       125                    130                   135 | 619 |
| gct gag aca gcc tgt agg cag atg ggc tac agc agc aaa ccc act ttc<br>Ala Glu Thr Ala Cys Arg Gln Met Gly Tyr Ser Ser Lys Pro Thr Phe<br>                    140                         145                    150 | 667 |
| aga gct gtg gag att ggc cca gac cag gat ctg gat gtt gtt gaa atc<br>Arg Ala Val Glu Ile Gly Pro Asp Gln Asp Leu Asp Val Val Glu Ile<br>                  155                    160                    165 | 715 |
| aca gaa aac agc cag gag ctt cgc atg cgg aac tca agt ggg ccc tgt<br>Thr Glu Asn Ser Gln Glu Leu Arg Met Arg Asn Ser Ser Gly Pro Cys<br>170                         175                    180 | 763 |
| ctc tca ggc tcc ctg gtc tcc ctg cac tgt ctt gcc tgt ggg aag agc<br>Leu Ser Gly Ser Leu Val Ser Leu His Cys Leu Ala Cys Gly Lys Ser<br>185                         190                    195 | 811 |
| ctg aag acc ccc cgt gtg gtg ggt ggg gag gag gcc tct gtg gat tct<br>Leu Lys Thr Pro Arg Val Val Gly Gly Glu Glu Ala Ser Val Asp Ser<br>200                         205                    210                    215 | 859 |
| tgg cct tgg cag gtc agc atc cag tac gac aaa cag cac gtc tgt gga<br>Trp Pro Trp Gln Val Ser Ile Gln Tyr Asp Lys Gln His Val Cys Gly<br>                    220                         225                    230 | 907 |
| ggg agc atc ctg gac ccc cac tgg gtc ctc acg gca gcc cac tgc ttc<br>Gly Ser Ile Leu Asp Pro His Trp Val Leu Thr Ala Ala His Cys Phe<br>                  235                    240                    245 | 955 |
| agg aaa cat acc gat gtg ttc aac tgg aag gtg cgg gca ggc tca gac<br>Arg Lys His Thr Asp Val Phe Asn Trp Lys Val Arg Ala Gly Ser Asp<br>                  250                    255                    260 | 1003 |
| aaa ctg ggc agc ttc cca tcc ctg gct gtg gcc aag atc atc atc att<br>Lys Leu Gly Ser Phe Pro Ser Leu Ala Val Ala Lys Ile Ile Ile Ile<br>265                         270                    275 | 1051 |
| gaa ttc aac ccc atg tac ccc aaa gac aat gac atc gcc ctc atg aag<br>Glu Phe Asn Pro Met Tyr Pro Lys Asp Asn Asp Ile Ala Leu Met Lys<br>280                         285                    290                   295 | 1099 |
| ctg cag ttc cca ctc act ttc tca ggc aca gtc agg ccc atc tgt ctg<br>Leu Gln Phe Pro Leu Thr Phe Ser Gly Thr Val Arg Pro Ile Cys Leu<br>                  300                    305                    310 | 1147 |
| ccc ttc ttt gat gag gag ctc act cca gcc acc cca ctc tgg atc att<br>Pro Phe Phe Asp Glu Glu Leu Thr Pro Ala Thr Pro Leu Trp Ile Ile<br>                  315                    320                    325 | 1195 |

```
gga tgg ggc ttt acg aag cag aat gga ggg aag atg tct gac ata ctg    1243
Gly Trp Gly Phe Thr Lys Gln Asn Gly Gly Lys Met Ser Asp Ile Leu
            330                 335                 340 ctg cag gcg tca gtc cag gtc att gac agc aca cgg tgc aat gca gac    1291
Leu Gln Ala Ser Val Gln Val Ile Asp Ser Thr Arg Cys Asn Ala Asp
345                 350                 355 gat gcg tac cag ggg gaa gtc acc gag aag atg atg tgt gca ggc atc    1339
Asp Ala Tyr Gln Gly Glu Val Thr Glu Lys Met Met Cys Ala Gly Ile
360                 365                 370                 375 ccg gaa ggg ggt gtg gac acc tgc cag ggt gac agt ggt ggg ccc ctg    1387
Pro Glu Gly Gly Val Asp Thr Cys Gln Gly Asp Ser Gly Gly Pro Leu
            380                 385                 390 atg tac caa tct gac cag tgg cat gtg gtg ggc atc gtt agc tgg ggc    1435
Met Tyr Gln Ser Asp Gln Trp His Val Val Gly Ile Val Ser Trp Gly
                395                 400                 405 tat ggc tgc ggg ggc ccg agc acc cca gga gta tac acc aag gtc tca    1483
Tyr Gly Cys Gly Gly Pro Ser Thr Pro Gly Val Tyr Thr Lys Val Ser
410                 415                 420 gcc tat ctc aac tgg atc tac aat gtc tgg aag gct gag ctg taa        1528
Ala Tyr Leu Asn Trp Ile Tyr Asn Val Trp Lys Ala Glu Leu
            425                 430                 435 tgctgctgcc ctttgcagt gctgggagcc gcttccttcc tgccctgccc acctggggat    1588
cccccaaagt cagacacaga gcaagagtcc ccttgggtac accccctctgc ccacagcctc   1648 agcatttctt ggagcagcaa agggcctcaa ttcctataag agaccctcgc agcccagagg    1708
cgcccagagg aagtcagcag ccctagctcg gccacacttg gtgctcccag catcccaggg    1768
agagacacag cccactgaac aaggtctcag gggtattgct aagccaagaa ggaacttttcc   1828 cacactactg aatggaagca ggctgtcttg taaaagccca gatcactgtg ggctggagag    1888
gagaaggaaa gggtctgcgc cagccctgtc cgttttcacc catccccaag cctactagag    1948
caagaaacca gttgtaatat aaaatgcact gccctactgt tggtatgact accgttacct    2008
actgttgtca ttgttattac agctatggcc actattatta aagagctgtg taacatttct    2068
ggcaaaaaaa aaa                                                     2081
```

<210> SEQ ID NO 8
<211> LENGTH: 437
<212> TYPE: PRT
<213> ORGANISM: Homo sapiens

<400> SEQUENCE: 8

```
Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
        35                  40                  45

Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
```

-continued

```
        115                 120                 125

Asp Asn Phe Thr Glu Ala Leu Ala Glu Thr Ala Cys Arg Gln Met Gly
    130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175

Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205

Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
    290                 295                 300

Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
            340                 345                 350

Ser Thr Arg Cys Asn Ala Asp Asp Ala Tyr Gln Gly Glu Val Thr Glu
        355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
            420                 425                 430

Trp Lys Ala Glu Leu
        435

<210> SEQ ID NO 9
<211> LENGTH: 5
<212> TYPE: PRT
<213> ORGANISM: Unknown
<220> FEATURE:
<223> OTHER INFORMATION: cytokine receptor extracellular motif found in
      many species
<221> NAME/KEY: MISC_FEATURE
<222> LOCATION: (3)..(3)
<223> OTHER INFORMATION: “Xaa” at position 3 can be any amino acid.

<400> SEQUENCE: 9

Trp Ser Xaa Trp Ser
1               5
```

METHODS OF DIAGNOSING AND DETERMINING PROGNOSIS OF COLORECTAL CANCER

This application is a continuation-in-part of U.S. Ser. No. 09/642,252 filed Aug. 17, 2000 now abandoned, and U.S. Ser. No. 09/656,002 filed Sep. 6, 2000, now U.S. Pat. No. 6,455,668.

FIELD OF THE INVENTION

The invention relates to the identification of expression profiles and the nucleic acids involved in colorectal cancer, and to the use of such expression profiles and nucleic acids in diagnosis and prognosis of colorectal cancer. The invention further relates to methods for identifying and using candidate agents and/or targets which modulate colorectal cancer.

BACKGROUND OF THE INVENTION

Colorectal cancer is a significant cancer in Western populations. It develops as the result of a pathologic transformation of normal colon epithelium to an invasive cancer. There have been a number of recently characterized genetic alterations that have been implicated in colorectal cancer, including mutations in two classes of genes, tumor-suppressor genes and proto-oncogenes, with recent work suggesting that mutations in DNA repair genes may also be involved in tumorigenesis. For example, inactivating mutations of both alleles of the adenomatous polyposis coli (APC) gene, a tumor suppressor gene, appears to be one of the earliest events in colorectal cancer, and may even be the initiating event. Other genes implicated in colorectal cancer include the MCC gene, the p53 gene, the DCC (deleted in colorectal carcinoma) gene and other chromosome 18 q genes, and genes in the TGF-β signalling pathway. For a review, see Molecular Biology of Colorectal Cancer, pp238–299, in Curr. Probl. Cancer, September/October 1997.

Imaging of colorectal cancer for diagnosis has been problematic and limited. In addition, dissemination of tumor cells (metastases) to locoregional lymph nodes is an important prognostic factor; five year survival rates drop from 80 percent in patients with no lymph node metastases to 45 to 50 percent in those patients who do have lymph node metastases. A recent report showed that micrometastases can be detected from lymph nodes using reverse transcriptase-PCR methods based on the presence of mRNA for carcinoembryonic antigen, which has previously been shown to be present in the vast majority of colorectal cancers but not in normal tissues. Liefers et al., New England J. of Med. 339(4):223 (1998).

Thus, methods that can be used for diagnosis and prognosis of colorectal cancer would be desirable. While academia and industry has made an effort to identify novel sequences, there has not been an equal effort exerted to identify the function of the novel sequences in disease states of concern, such as cancer. For example, databases show the sequence for accession numbers AA331393, N95719, Al1346620, AA411502, and AF179224, and the later has been identified as a transmembrane serine protease 3, but there is limited data correlating these sequences with a disease state. Further provided are methods that can be used to screen candidate bioactive agents for the ability to modulate colorectal cancer. Additionally, provided herein are molecular targets for therapeutic intervention in colorectal and other cancers.

SUMMARY OF THE INVENTION

The present invention provides methods for screening for compositions which modulate colorectal cancer. In one aspect, a method of screening drug candidates comprises providing a cell that expresses an expression profile gene or fragments thereof. Preferred embodiments of the expression profile genes as described herein include the sequence comprising CGA7, or a fragment thereof. Other preferred embodiments include the sequence comprising CJA8, or a fragment thereof. The method further includes adding a drug candidate to the cell and determining the effect of the drug candidate on the expression of the expression profile gene.

In one embodiment, the method of screening drug candidates includes comparing the level of expression in the absence of the drug candidate to the level of expression in the presence of the drug candidate, wherein the concentration of the drug candidate can vary when present, and wherein the comparison can occur after addition or removal of the drug candidate. In a preferred embodiment, the cell expresses at least two expression profile genes. The profile genes may show an increase or decrease.

Also provided herein is a method of screening for a bioactive agent capable of binding to a colorectal cancer modulating protein (CCMP) or a fragment thereof, the method comprising combining the CCMP or fragment thereof and a candidate bioactive agent, and determining the binding of the candidate agent to the CCMP or fragment thereof. In a preferred embodiment, the CCMP is CGA7. In another preferred embodiment, the CCMP is CJA8.

Further provided herein is a method for screening for a bioactive agent capable of modulating the bioactivity of a CCMP or a fragment thereof. In one embodiment, the method comprises combining the CCMP or fragment thereof and a candidate bioactive agent, and determining the effect of the candidate agent on the bioactivity of the CCMP or the fragment thereof. In a preferred embodiment, the CCMP is CGA7. In another preferred embodiment, the CCMP is CJA8.

Also provided herein is a method of evaluating the effect of a candidate colorectal cancer drug comprising administering the drug to a transgenic animal expressing or overexpressing a CCMP or a fragment thereof, or an animal lacking a CCMP for example as a result of a gene knockout. In a preferred embodiment, the CCMP is CGA7. In another preferred embodiment, the CCMP is CJA8.

Additionally, provided herein is a method of evaluating the effect of a candidate colorectal cancer drug comprising administering the drug to a patient and removing a cell sample from the patient. The expression profile of the cell is then determined. This method may further comprise comparing the expression profile to an expression profile of a healthy individual.

Furthermore, a method of diagnosing colorectal cancer is provided. The method comprises determining the expression of a gene which encodes CGA7 or a fragment thereof, in a first tissue type of a first individual, and comparing this to the expression of the gene from a second unaffected individual. A difference in the expression indicates that the first individual has colorectal cancer.

In another embodiment, the method comprises determining the expression of a gene which encodes CJA8 or a fragment thereof, in a first tissue type of a first individual and comparing this to the expression of the gene from a second unaffected individual. A difference in the expression indicates that the first individual has colorectal cancer.

In another aspect, the present invention provides an antibody which specifically binds to CGA7, or a fragment thereof. Preferably the antibody is a monoclonal antibody. The antibody can be a fragment of an antibody such as a single stranded antibody as further described herein, or can be conjugated to another molecule. In one embodiment, the antibody is a humanized antibody.

In another aspect, the present invention provides an antibody which specifically binds to CJA8, or a fragment thereof. Preferably the antibody is a monoclonal antibody. The antibody can be a fragment of an antibody such as a single stranded antibody as further described herein, or can be conjugated to another molecule. In one embodiment, the antibody is a humanized antibody.

In one embodiment a method for screening for a bioactive agent capable of interfering with the binding of CGA7 or a fragment thereof and an antibody which binds to said CGA7 or fragment thereof is provided. In a preferred embodiment, the method comprises combining CGA7 or a fragment thereof, a candidate bioactive agent and an antibody which binds to said CGA7 or fragment thereof. The method further includes determining the binding of said CGA7 or fragment thereof and said antibody. Wherein there is a change in binding, an agent is identified as an interfering agent. The interfering agent can be an agonist or an antagonist. Preferably, the antibody as well as the agent inhibits colorectal cancer.

In another embodiment a method for screening for a bioactive agent capable of interfering with the binding of CJA8 or a fragment thereof and an antibody which binds to said CJA8 or fragment thereof is provided. In a preferred embodiment, the method comprises combining CJA8 or a fragment thereof, a candidate bioactive agent and an antibody which binds to said CJA8 or fragment thereof. The method further includes determining the binding of said CJA8 or fragment thereof and said antibody. Wherein there is a change in binding, an agent is identified as an interfering agent. The interfering agent can be an agonist or an antagonist. Preferably, the antibody as well as the agent inhibits colorectal cancer.

In one aspect of the invention, a method for inhibiting the activity of a colorectal cancer modulating protein are provided. The method comprises binding an inhibitor to the protein. In a preferred embodiment, the protein is CGA7. In another preferred embodiment, the protein is CJA8.

In another aspect, the invention provides a method for neutralizing the effect of a colorectal cancer modulating protein. The method comprises contacting an agent specific for the protein with the protein in an amount sufficient to effect neutralization. In a preferred embodiment, the protein is CGA7. In another preferred embodiment, the protein is CJA8.

In a further aspect, a method for treating or inhibiting colorectal cancer is provided. In one embodiment, the method comprises administering to a cell a composition comprising an antibody to CGA7 or a fragment thereof. In another embodiment, the method comprises administering to a cell a composition comprising an antibody to CJA8 or a fragment thereof. In one embodiment, the antibody is conjugated to a therapeutic moiety. Such therapeutic moieties include a cytotoxic agent and a radioisotope. The method can be performed in vitro or in vivo, preferably in vivo to an individual. In a preferred embodiment the method of inhibiting colorectal cancer is provided to an individual with such cancer.

As described herein, methods of treating or inhibiting colorectal cancer can be performed by administering an inhibitor of CGA7 activity to a cell or individual. In one embodiment, a CGA7 inhibitor is an antisense molecule to a nucleic acid encoding CGA7. Alternatively, methods of treating or inhibiting colorectal cancer can be performed by administering an inhibitor of CJA8 activity to a cell or individual. In one embodiment, a CJA8 inhibitor is an antisense molecule to a nucleic acid encoding CJA8.

Moreover, provided herein is a biochip comprising a nucleic acid segment which encodes CGA7, or a fragment thereof, wherein the biochip comprises fewer than 1000 nucleic acid probes. Also provided herein is a biochip comprising a nucleic acid segment which encodes CJA8, or a fragment thereof, wherein the biochip comprises fewer than 1000 nucleic acid probes. Preferably a biochip includes at least two nucleic acid segments.

Also provided herein are methods of eliciting an immune response in an individual. In one embodiment a method provided herein comprises administering to an individual a composition comprising CGA7 or a fragment thereof. In another aspect, said composition comprises a nucleic acid comprising a sequence encoding CGA7 or a fragment thereof.

In another embodiment a method provided herein comprises administering to an individual a composition comprising CJA8 or a fragment thereof. In another aspect, said composition comprises a nucleic acid comprising a sequence encoding CJA8 or a fragment thereof.

Further provided herein are compositions capable of eliciting an immune response in an individual. In one embodiment, a composition provided herein comprises CGA7 or a fragment thereof and a pharmaceutically acceptable carrier. In another embodiment, said composition comprises a nucleic acid comprising a sequence encoding CGA7 or a fragment thereof and a pharmaceutically acceptable carrier.

In one embodiment, a composition provided herein comprises CJA8 or a fragment thereof and a pharmaceutically acceptable carrier. In another embodiment, said composition comprises a nucleic acid comprising a sequence encoding CJA8 or a fragment thereof and a pharmaceutically acceptable carrier.

Other aspects of the invention will become apparent to the skilled artisan by the following description of the invention.

DETAILED DESCRIPTION OF THE FIGURES

FIG. 1 (SEQ ID NO: 1) shows an embodiment of a nucleic acid (mRNA) which includes a sequence which encodes a colorectal cancer protein provided herein, CGA7.

FIG. 2 (SEQ ID NO: 2) shows an embodiment of an amino acid sequence of CGA7, encoded by the nucleic acid of FIG. 1 (SEQ ID NO: 1).

FIG. 3 (SEQ ID NO: 3) shows a preferred embodiment of a nucleic acid (mRNA) which includes a sequence which encodes CGA7. The start (ATG) and stop (TAG) codons are shaded. The sequence of Accession Number AA331393 appears in bold. The sequence of Accession Number Al1346620 is underlined. Sequence corresponding to Accession Number N95719 is shown in italics.

FIG. 4 (SEQ ID NO: 4) shows a preferred embodiment of an amino acid sequence of CGA7, encoded by the nucleic acid of FIG. 3 (SEQ ID NO: 3).

FIG. 5 (SEQ ID NO: 5) shows an embodiment of a nucleic acid (mRNA) which includes a sequence which encodes a colorectal cancer protein provided herein, CJA8.

FIG. 6 (SEQ ID NO: 6) shows an embodiment of an amino acid sequence of CJA8, encoded by the nucleic acid of FIG. 5 (SEQ ID NO: 5). A putative transmembrane region is shaded.

FIG. 7 (SEQ ID NO: 7) shows a preferred embodiment of a nucleic acid (mRNA) which includes a sequence which encodes a colorectal cancer protein provided herein, CJA8. CJA8 is encoded by the nucleic acid of Accession Number AF179224. The start (ATG) and stop (TM) codons shaded. Sequence overlapping with Accession Number AA411502 is underlined. Sequence in italics corresponds to the in silico generated contig sequence.

FIG. 8 (SEQ ID NO: 8) shows a preferred embodiment of an amino acid sequence of CJA8, encoded by the nucleic acid of FIG. 7 (SEQ ID NO: 7). A putative transmembrane region is shaded.

DETAILED DESCRIPTION OF THE INVENTION

The present invention provides novel methods for diagnosis and prognosis evaluation for colorectal cancer, as well as methods for screening for compositions which modulate colorectal cancer and compositions which bind to modulators of colorectal cancer. In one aspect, the expression levels of genes are determined in different patient samples for which either diagnosis or prognosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is unique to the state of the cell. That is, normal tissue may be distinguished from colorectal cancer tissue, and within colorectal cancer tissue, different prognosis states (good or poor long term survival prospects, for example) may be determined. By comparing expression profiles of colorectal cancer tissue in different states, information regarding which genes are important (including both up- and down-regulation of genes) in each of these states is obtained. The identification of sequences that are differentially expressed in colorectal cancer tissue versus normal colon tissue, as well as differential expression resulting in different prognostic outcomes, allows the use of this information in a number of ways. For example, the evaluation of a particular treatment regime may be evaluated: does a chemotherapeutic drug act to improve the long-term prognosis in a particular patient. Similarly, diagnosis may be done or confirmed by comparing patient samples with the known expression profiles. Furthermore, these gene expression profiles (or individual genes) allow screening of drug candidates with an eye to mimicking or altering a particular expression profile; for example, screening can be done for drugs that suppress the colorectal cancer expression profile or convert a poor prognosis profile to a better prognosis profile. This may be done by making biochips comprising sets of the important colorectal cancer genes, which can then be used in these screens. These methods can also be done on the protein basis; that is, protein expression levels of the colorectal cancer proteins can be evaluated for diagnostic and prognostic purposes or to screen candidate agents. In addition, the colorectal cancer nucleic acid sequences can be administered for gene therapy purposes, including the administration of antisense nucleic acids, or the colorectal cancer proteins (including antibodies and other modulators thereof) administered as therapeutic drugs.

Thus the present invention provides nucleic acid and protein sequences that are differentially expressed in colorectal cancer when compared to normal tissue. The differentially expressed sequences provided herein are termed "colorectal cancer sequences". As outlined below, colorectal cancer sequences include those that are up-regulated (i.e. expressed at a higher level) in colorectal cancer, as well as those that are down-regulated (i.e. expressed at a lower level) in colorectal cancer. In a preferred embodiment, the colorectal cancer sequences are from humans; however, as will be appreciated by those in the art, colorectal cancer sequences from other organisms may be useful in animal models of disease and drug evaluation; thus, other colorectal cancer sequences are provided, from vertebrates, including mammals, including rodents (rats, mice, hamsters, guinea pigs, etc.), primates, farm animals (including sheep, goats, pigs, cows, horses, etc). Colorectal cancer sequences from other organisms may be obtained using the techniques outlined below.

In one embodiment, the colorectal cancer sequences encode CGA7, or fragments thereof. In a specific embodiment, the gene encoding the CGA7 colorectal cancer sequence comprises the sequence depicted in FIG. 1 (SEQ ID NO: 1), or a fragment thereof. In a preferred embodiment, the colorectal cancer sequence comprises residues 11–641 and 755–1007 of FIG. 1 (SEQ ID NO: 1), or a fragment thereof. In another preferred embodiment, a gene encoding the CGA7 colorectal cancer sequence is that depicted in FIG. 3 (SEQ ID NO: 3), or a fragment thereof.

In one embodiment, the colorectal cancer sequences encode a protein comprising the amino acid sequence depicted in FIG. 2 (SEQ ID NO: 2), or a fragment thereof. In a preferred embodiment, the colorectal cancer sequences encode a protein comprising residues 1–198 and 235–320 of the amino acid sequence depicted in FIG. 2 (SEQ ID NO: 2), or a fragment thereof. In a more preferred embodiment, the colorectal cancer sequences encode a protein having the amino acid sequence depicted in FIG. 4 (SEQ ID NO: 4), or a fragment thereof.

In a preferred embodiment, the colorectal cancer sequences encode CJA8, or fragments thereof. In one embodiment, the colorectal cancer sequence comprises the sequence depicted in FIG. 5 (SEQ ID NO: 5), or a fragment thereof. In a preferred embodiment, the colorectal cancer sequence is that depicted in FIG. 7 (SEQ ID NO: 7), or a fragment thereof. In one embodiment, the colorectal cancer sequences encode a protein comprising the amino acid sequence depicted in FIG. 6 (SEQ ID NO: 6), or a fragment thereof. In a preferred embodiment, the colorectal cancer sequences encode a protein having the amino acid sequence depicted in FIG. 8 (SEQ ID NO: 8), or a fragment thereof. In a preferred embodiment, CJA8 has the sequence of a a transmembrane serine protease 3.

Colorectal cancer sequences can include both nucleic acid and amino acid sequences. In a preferred embodiment, the colorectal cancer sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a colorectal cancer protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the colorectal cancer sequences are nucleic acids. As will be appreciated by those in the art and is more fully outlined below, colorectal cancer sequences are useful in a variety of applications, including diagnostic applications, which will detect naturally occurring nucleic acids, as well as screening applications; for example, biochips comprising nucleic acid probes to the colorectal cancer sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramidate (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp169–176). Several nucleic acid analogs are described in Rawls, C & E News June 2, 1997 page 35. All of these references are hereby expressly incorporated by reference. These modifications of the ribose-phosphate backbone may be done for a variety of reasons, for example to increase the stability and half-life of such molecules in physiological environments or as probes on a biochip.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

A colorectal cancer sequence can be initially identified by substantial nucleic acid and/or amino acid sequence homology to the colorectal cancer sequences outlined herein. Such homology can be based upon the overall nucleic acid or amino acid sequence, and is generally determined as outlined below, using either homology programs or hybridization conditions.

The colorectal cancer sequences of the invention can be identified as follows. Samples of normal and tumor tissue are applied to biochips comprising nucleic acid probes. The samples are first microdissected, if applicable, and treated as is known in the art for the preparation of mRNA. Suitable biochips are commercially available, for example from Affymetrix. Gene expression profiles as described herein are generated, and the data analyzed.

In a preferred embodiment, the genes showing changes in expression as between normal and disease states are compared to genes expressed in other normal tissues, including, but not limited to lung, heart, brain, liver, breast, colorectal, kidney, muscle, prostate, small intestine, large intestine, spleen, bone, and placenta. In a preferred embodiment, those genes identified during the colorectal cancer screen that are expressed in any significant amount in other tissues are removed from the profile, although in some embodiments, this is not necessary. That is, when screening for drugs, it is preferable that the target be disease specific, to minimize possible side effects.

In a preferred embodiment, colorectal cancer sequences are those that are up-regulated in colorectal cancer; that is, the expression of these genes is higher in colorectal carcinoma as compared to normal colon tissue. "Up-regulation" as used herein means at least about a 50% increase, preferably a two-fold change, more preferably at least about a three fold change, with at least about five-fold or higher being preferred. All accession numbers herein are for the GenBank sequence database and the sequences of the accession numbers are hereby expressly incorporated by reference. GenBank is known in the art, see, e.g., Benson, DA, et al., Nucleic Acids Research 26:1–7 (1998) and http://www.ncbi.nlm.nih.gov/. In addition, these genes are found to be expressed in a limited amount or not at all in bladder, bone marrow, brain, breast, fibroblasts, heart, kidney, liver, lung, muscle, pancreas, prostate, skin, small intestine, spleen, stomach and testes.

In a preferred embodiment, the gene for CGA7 or CJA8 is up-regulated in colorectal cancer tissue as compared with normal colon tissue.

In another embodiment, colorectal cancer sequences are those that are down-regulated in colorectal cancer; that is, the expression of these genes is lower in, for example, colorectal carcinoma as compared to normal colon tissue. "Down-regulation" as used herein means at least about a two-fold change, preferably at least about a three fold change, with at least about five-fold or higher being preferred.

Colorectal cancer proteins of the present invention may be classified as secreted proteins, transmembrane proteins or intracellular proteins. In a preferred embodiment the colorectal cancer protein is an intracellular protein. Intracellular proteins may be found in the cytoplasm and/or in the nucleus and may be associated with the plasma membrane. Intracellular proteins are involved in all aspects of cellular function and replication (including, for example, signaling pathways); aberrant expression of such proteins results in unregulated or disregulated cellular processes. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

An increasingly appreciated concept in characterizing intracellular proteins is the presence in the proteins of one or more motifs for which defined functions have been attributed. In addition to the highly conserved sequences found in the enzymatic domain of proteins, highly conserved sequences have been identified in proteins that are involved in protein—protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein—protein interactions. Some of these may also be involved in binding to phospholipids or other second messengers. As will be appreciated by one of ordinary skill in the art, these motifs can be identified on the basis of primary sequence; thus, an analysis of the sequence of proteins may provide insight into both the enzymatic potential of the molecule and/or molecules with which the protein may associate.

In a preferred embodiment, CGA7 is an intracellular protein. Preferably, CGA7 is primarily located in the nucleus.

In a preferred embodiment, the colorectal cancer sequences are transmembrane proteins. Transmembrane proteins are molecules that span the phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles.

For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors are classified as "seven transmembrane domain" proteins, as they contain 7 membrane spanning regions. Important transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Characteristics of transmembrane domains include approximately 20 consecutive hydrophobic amino acids that may be followed by charged amino acids. Therefore, upon analysis of the amino acid sequence of a particular protein, the localization and number of transmembrane domains within the protein may be predicted.

The extracellular domains of transmembrane proteins are diverse; however, conserved motifs are found repeatedly among various extracellular domains. Conserved structure and/or functions have been ascribed to different extracellular motifs. For example, cytokine receptors are characterized by a cluster of cysteines and a WSXWS (W=tryptophan, S=serine, X=any amino acid) motif (SEQ ID NO: 9). Immunoglobulin-like domains are highly conserved. Mucin-like domains may be involved in cell adhesion and leucine-rich repeats participate in protein—protein interactions.

Many extracellular domains are involved in binding to other molecules. In one aspect, extracellular domains are receptors. Factors that bind the receptor domain include circulating ligands, which may be peptides, proteins, or small molecules such as adenosine and the like. For example, growth factors such as EGF, FGF and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell—cell interactions. Cell-associated ligands can be tethered to the cell for example via a glycosylphosphatidylinositol (GPI) anchor, or may themselves be transmembrane proteins. Extracellular domains also associate with the extracellular matrix and contribute to the maintenance of the cell structure.

Colorectal cancer proteins that are transmembrane are particularly preferred in the present invention as they are good targets for immunotherapeutics, as are described herein. In addition, as outlined below, transmembrane proteins can be also useful in imaging modalities.

In a preferred embodiment, CJA8 is a transmembrane protein. In a preferred embodiment, CJA8 is expressed at the plasma membrane surface.

It will also be appreciated by those in the art that a transmembrane protein can be made soluble by removing transmembrane sequences, for example through recombinant methods. Furthermore, transmembrane proteins that have been made soluble can be made to be secreted through recombinant means by adding an appropriate signal sequence.

In a preferred embodiment, the colorectal cancer proteins are secreted proteins; the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in close proximity to the cell that secreted the factor) or an endocrine manner (acting on cells at a distance). Thus secreted molecules find use in modulating or altering numerous aspects of physiology. Colorectal cancer proteins that are secreted proteins are particularly preferred in the present invention as they serve as good targets for diagnostic markers, for example for blood tests.

A colorectal cancer sequence is initially identified by substantial nucleic acid and/or amino acid sequence homology to the colorectal cancer sequences outlined herein. Such homology can be based upon the overall nucleic acid or amino acid sequence, and is generally determined as outlined below, using either homology programs or hybridization conditions.

As used herein, a nucleic acid is a "colorectal cancer nucleic acid" on the basis of sequence homology determined by comparison of a subject sequence to the nucleic acid sequence of FIG. 1 (SEQ ID NO:1) or FIG. 3 (SEQ ID NO:3), or to a nucleic acid sequence encoding the amino acid sequence of FIG. 2 (SEQ ID NO:2) or FIG. 4 (SEQ ID NO:4). A nucleic acid is also a "colorectal cancer nucleic acid" on the basis of sequence homology determined by comparison of a subject sequence to the nucleic acid sequence of FIG. 5 (SEQ ID NO: 5) or FIG. 7 (SEQ ID NO: 7), or to a nucleic acid sequence encoding the amino acid sequence of FIG. 6 (SEQ ID NO: 6) or FIG. 8 (SEQ ID NO: 8). Homology in this context means sequence identity. Therefore, a nucleic acid is a "colorectal cancer nucleic acid" if the overall identity of the nucleic acid sequence to the nucleic acid sequence of FIG. 1 (SEQ ID NO: 1), FIG. 3 (SEQ ID NO: 3), FIG. 5 (SEQ ID NO: 5), or FIG. 7 (SEQ ID NO: 7), or to a nucleic acid sequence encoding the amino acid sequence of FIG. 2 (SEQ ID NO: 2), FIG. 4 (SEQ ID NO: 4), FIG. 6 (SEQ ID NO: 6), or FIG. 8 (SEQ ID NO: 8) is preferably greater than about 75%, more preferably greater than about 80%, even more preferably greater than about 85% and most preferably greater than 90%. In some embodiments the identity will be as high as about 93 to 95 or 98%. Percent nucleic acid identity is further defined below.

A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection.

In a preferred embodiment, the sequences which are used to determine sequence identity or similarity are selected from the sequences set forth in the figures, preferably the sequence of FIG. 3 (SEQ ID NO: 3), and fragments thereof. In another preferred embodiment, the sequence used to determine sequence identity or similarity is the sequence of FIG. 7 (SEQ ID NO: 7), and fragments thereof.

In one embodiment the sequences utilized herein are those set forth in the figures. In another embodiment, the sequences are naturally occurring allelic variants of the sequences set forth in the figures. In another embodiment, the sequences are sequence variants as further described herein.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266: 460–480 (1996) [http://blast.wustl/edu/blast/READ.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of FIG. 1 (SEQ ID NO: 1), FIG. 3 (SEQ ID NO: 3), FIG. 5 (SEQ ID NO: 5) or FIG. 7 (SEQ ID NO: 7), determined by the method utilizing the BLASTN module of the BLAST-2.1 program BLAST-2.1 program (publicly available on the NCBI web site at www.ncbi.nim.nih.gov/BLAST/) set to the default parameters (cost to open a gap: 5; cost to extend a gap: 2; penalty for a mismatch: -3; reward for a match: 1; expectation value: 10.0; word size: 11; matrix: BLOSUM62; gap existence cost: 11; per residue gap cost: 1; lambda ratio: 0.84; filter: low complexity). However, the skilled artisan will appreciate that a similar determination may be made using any means of nucleic acid sequence comparison described herein or known in the art.

The alignment may include the introduction of gaps in the sequences to be aligned. In addition, for sequences which contain either more or fewer nucleosides than those of FIG. 1 (SEQ ID NO: 1), FIG. 3 (SEQ ID NO: 3), FIG. 5 (SEQ ID NO: 5) or FIG. 7 (SEQ ID NO: 7), it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the nucleic acid homology is determined through hybridization studies. Thus, for example, nucleic acids which hybridize under high stringency to the nucleic acid sequences which encode the peptides identified in FIG. 2 (SEQ ID NO: 2), FIG. 4 (SEQ ID NO: 4), FIG. 6 (SEQ ID NO: 6) or FIG. 8 (SEQ ID NO: 8), or their complements, are considered colorectal cancer sequences. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology--Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, the colorectal cancer nucleic acid sequences of the invention are fragments of larger genes, i.e. they are nucleic acid segments. "Genes" in this context includes coding regions, non-coding regions, and mixtures of coding and non-coding regions. Accordingly, as will be appreciated by those in the art, using the sequences provided herein, additional sequences of the colorectal cancer genes can be obtained, using techniques well known in the art for cloning either longer sequences or the full length sequences; see Maniatis et al., and Ausubel, et al., supra, hereby expressly incorporated by reference.

Once the colorectal cancer nucleic acid is identified, it can be cloned and, if necessary, its constituent parts recombined to form the entire colorectal cancer nucleic acid. Once isolated from its natural source, e.g., contained within a plasmid or other vector or excised therefrom as a linear nucleic acid segment, the recombinant colorectal cancer nucleic acid can be further-used as a probe to identify and isolate other colorectal cancer nucleic acids, for example additional coding regions. It can also be used as a "precursor" nucleic acid to make modified or variant colorectal cancer nucleic acids and proteins.

The colorectal cancer nucleic acids of the present invention are used in several ways. In a first embodiment, nucleic acid probes to the colorectal cancer nucleic acids are made and attached to biochips to be used in screening and diagnostic methods, as outlined below, or for administration, for example for gene therapy and/or antisense applications. Alternatively, the colorectal cancer nucleic acids that include coding regions of colorectal cancer proteins can be put into expression vectors for the expression of colorectal cancer proteins, again either for screening purposes or for administration to a patient.

In a preferred embodiment, nucleic acid probes to colorectal cancer nucleic acids (both the nucleic acid sequences encoding peptides outlined in the figures and/or the complements thereof are made. The nucleic acid probes attached to the biochip are designed to be substantially complementary to the colorectal cancer nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluorescese. A preferred substrate is described in copending application entitled Reusable Low Fluorescent Plastic Biochip filed March 15, 1999, herein incorporated by reference in its entirety.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChipTM technology.

In a preferred embodiment, colorectal cancer nucleic acids encoding colorectal cancer proteins are used to make a variety of expression vectors to express colorectal cancer proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the colorectal cancer protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the colorectal cancer protein; for example, transcriptional and translational regulatory nucleic acid sequences from Bacillus are preferably used to express the colorectal cancer protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The colorectal cancer proteins of the present invention are produced by culturing a host cell transformed with an expression vector containing nucleic acid encoding a colorectal cancer protein, under the appropriate conditions to induce or cause expression of the colorectal cancer protein. The conditions appropriate for colorectal cancer protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli, Bacillus subtilis,* Sf9 cells, C129 cells, 293 cells, Neurospora, BHK, CHO, COS, HeLa cells, THP1 cell line (a macrophage cell line) and human cells and cell lines.

In a preferred embodiment, the colorectal cancer proteins are expressed in mammalian cells. Mammalian expression systems are also known in the art, and include retroviral systems. A preferred expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, colorectal cancer proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the colorectal cancer protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris,* and *Streptococcus lividans,* among others. The bacterial expression vectors are transformed into bacterial host cells using techniques well known in the art, such as calcium chloride treatment, electroporation, and others.

In one embodiment, colorectal cancer proteins are produced in insect cells. Expression vectors for the transformation of insect cells, and in particular, baculovirus-based expression vectors, are well known in the art.

In a preferred embodiment, colorectal cancer protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.*

The colorectal cancer protein may also be made as a fusion protein, using techniques well known in the art. Thus, for example, for the creation of monoclonal antibodies, if the desired epitope is small, the colorectal cancer protein may be fused to a carrier protein to form an immunogen. Alternatively, the colorectal cancer protein may be made as a fusion protein to increase expression, or for other reasons. For example, when the colorectal cancer protein is a colorectal cancer peptide, the nucleic acid encoding the peptide may be linked to other nucleic acid for expression purposes.

In one embodiment, the colorectal cancer nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the colorectal cancer nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Accordingly, the present invention also provides colorectal cancer protein sequences. A colorectal cancer protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the colorectal cancer protein has homology to some protein in the database being used. In one aspect, a protein is a "colorectal cancer protein" if the overall identity of the amino acid sequence to the amino acid sequence of FIG. 4 (SEQ ID NO: 4) or FIG. 8 (SEQ ID NO: 8) is preferably greater than about 75%, more preferably greater than about 80%, even more preferably greater than about 85% and most preferably greater than 90%. In some embodiments the identity will be as high as about 93 to 95 or 98%. In another aspect, a protein is a "colorectal cancer protein" if the overall similarity of the amino acid sequence to the amino acid sequence of FIG. 4 (SEQ ID NO: 4) or FIG. 8 (SEQ ID NO: 8) is preferably greater than about 75%, more preferably greater than about 80%, even more preferably greater than about 85%, still more preferably greater than 90% and most preferably greater than 95%. In some embodiments the similarity will be as high as about 96 to 99 or 100%. Percent identity and percent similarity of proteins are further defined below.

As one approach to identifying colorectal cancer proteins, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "Query Genetic Codes" is standard (1). The matrix is BLOSUM62; gap existence cost is 11, per residue gap cost is 1; and the lambda ratio is 0.85 default. This results in the generation of a putative protein sequence.

In another approach, a colorectal cancer protein is identified based on homology between an amino acid sequence disclosed herein and one or more amino acid sequences provided, for example those provided in the GenBank database. In this case, homology is determined by comparison of the amino acid sequences. As used herein, "protein identity", "amino acid sequence identity", and grammatical equivalents thereof means the number of identical residues when two sequences are compared using the BLASTP module of the BLAST-2.1 program (publicly available on the NCBI web site at www.ncbi.nim.nih.gov/BLASTI) and default settings (expectation value: 10.0; filter: low complexity; gap existence cost: 11; per residue gap cost: 1; lambda ratio: 0.84). Similarity is based on the conservation of amino acid residues in a sequence alignment, wherein the aligned residues are identical or have similar physico-chemical properties. Examples of residues with similar physico-chemical properties are found on the table of conserved amino acid substitutions below (Chart 1). As used herein, "percent similarity" is the percent "positives" identified using the BLAST-2.1 program as described above. However, the skilled artisan will appreciate that similar determinations may be made using any of several other methods described herein or known in the art.

Also included within one embodiment of colorectal cancer proteins are amino acid variants of the naturally occurring sequences, as determined herein. Preferably, the variants are greater than about 75% identical to the wild-type sequence, more preferably greater than about 80%, even more preferably greater than about 85% and most preferably greater than 90%. In some embodiments the identity will be as high as about 93 to 95 or 98%. In another embodiment, colorectal cancer proteins are amino acid variants of the naturally occurring sequences having preferably greater than about 75% similarity, more preferably greater than about 80%, even more preferably greater than about 85%, still more preferably greater than 90% and most preferably greater than 95%. In some embodiments the similarity will be as high as about 96 to 99 or 100%. This homology will be determined using standard techniques known in the art as are outlined above.

Colorectal cancer proteins of the present invention may be shorter or longer than the wild type amino acid sequences. Thus, in a preferred embodiment, included within the definition of colorectal cancer proteins are portions or fragments of the wild type sequences herein. In addition, as outlined above, the colorectal cancer nucleic acids of the invention may be used to obtain additional coding regions, and thus additional protein sequence, using techniques known in the art.

In a preferred embodiment, the colorectal cancer proteins are derivative or variant colorectal cancer proteins as compared to the wild-type sequence. That is, as outlined more fully below, the derivative colorectal cancer peptide will contain at least one amino acid substitution, deletion or insertion, with amino acid substitutions being particularly preferred. The amino acid substitution, insertion or deletion may occur at any residue within the colorectal cancer peptide.

Also included in an embodiment of colorectal cancer proteins of the present invention are amino acid sequence variants. These variants fall into one or more of three classes: substitutional, insertional or deletional variants. These variants ordinarily are prepared by site specific mutagenesis of nucleotides in the DNA encoding the colorectal cancer protein, using cassette or PCR mutagenesis or other techniques well known in the art, to produce DNA encoding the variant, and thereafter expressing the DNA in recombinant cell culture as outlined above. However, variant colorectal cancer protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the colorectal cancer protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed colorectal cancer variants screened for the optimal combination of desired activity.

Techniques for making substitution mutations at predetermined sites in DNA having a known sequence are well known, for example, M13 primer mutagenesis and PCR mutagenesis. Screening of the mutants is done using assays of colorectal cancer protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the colorectal cancer protein are desired, substitutions are generally made in accordance with the following chart:

CHART 1

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |

CHART 1-continued

| Original Residue | Exemplary Substitutions |
| --- | --- |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the colorectal cancer proteins as needed. Alternatively, the variant may be designed such that the biological activity of the colorectal cancer protein is altered. For example, glycosylation sites may be altered or removed.

Covalent modifications of colorectal cancer polypeptides are included within the scope of this invention. One type of covalent modification includes reacting targeted amino acid residues of a colorectal cancer polypeptide with an organic derivatizing agent that is capable of reacting with selected side chains or the N- or C-terminal residues of a colorectal cancer polypeptide. Derivatization with bifunctional agents is useful, for instance, for crosslinking colorectal cancer to a water-insoluble support matrix or surface for use in the method for purifying anti-colorectal cancer antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the a-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the colorectal cancer polypeptide included within the scope of this invention comprises altering the native glycosylation pattern of the polypeptide. "Altering the native glycosylation pattern" is intended for purposes herein to mean deleting one or more carbohydrate moieties found in native sequence colorectal cancer polypeptide, and/or adding one or more glycosylation sites that are not present in the native sequence colorectal cancer polypeptide.

Addition of glycosylation sites to colorectal cancer polypeptides may be accomplished by altering the amino acid sequence thereof. The alteration may be made, for example, by the addition of, or substitution by, one or more serine or threonine residues to the native sequence colorectal cancer polypeptide (for O-linked glycosylation sites). The colorectal cancer amino acid sequence may optionally be altered through changes at the DNA level, particularly by mutating the DNA encoding the colorectal cancer polypeptide at preselected bases such that codons are generated that will translate into the desired amino acids.

Another means of increasing the number of carbohydrate moieties on the colorectal cancer polypeptide is by chemical or enzymatic coupling of glycosides to the polypeptide. Such methods are described in the art, e.g., in WO 87/05330 published Sep. 11, 1987, and in Aplin and Wriston, Crit. Rev. Biochem., pp. 259–306 (1981).

Removal of carbohydrate moieties present on the colorectal cancer polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 18:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of colorectal cancer protein comprises linking the colorectal cancer polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Colorectal cancer polypeptides of the present invention may also be modified in a way to form chimeric molecules comprising a colorectal cancer polypeptide fused to another, heterologous polypeptide or amino acid sequence. In one embodiment, such a chimeric molecule comprises a fusion of a colorectal cancer polypeptide with a tag polypeptide which provides an epitope to which an anti-tag antibody can selectively bind. The epitope tag is generally placed at the amino-or carboxyl-terminus of the colorectal cancer polypeptide. The presence of such epitope-tagged forms of a colorectal cancer polypeptide can be detected using an antibody against the tag polypeptide. Also, provision of the epitope tag enables the colorectal cancer polypeptide to be readily purified by affinity purification using an anti-tag antibody or another type of affinity matrix that binds to the epitope tag. In an alternative embodiment, the chimeric molecule may comprise a fusion of a colorectal cancer polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 3610–3616 (1985)]; and the Herpes Simplex virus glycoprotein D (gD) tag and its antibody [Paborsky et al., Protein Engineering, 3(6): 547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:63936397 (1990)].

Also included with the definition of colorectal cancer protein in one embodiment are other colorectal cancer proteins of the colorectal cancer family, and colorectal cancer proteins from other organisms, which are cloned and expressed as outlined below. Thus, probe or degenerate polymerase chain reaction (PCR) primer sequences may be used to find other related colorectal cancer proteins from humans or other organisms. As will be appreciated by those in the art, particularly useful probe and/or PCR primer sequences include the unique areas of the colorectal cancer nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, colorectal cancer proteins can be made that are longer than those depicted in the figures, for example, by the elucidation of additional sequences, the addition of epitope or purification tags, the addition of other fusion sequences, etc.

Colorectal cancer proteins may also be identified as being encoded by colorectal cancer nucleic acids. Thus, colorectal cancer proteins are encoded by nucleic acids that will hybridize to the sequences of the sequence listings, or their complements, as outlined herein.

In a preferred embodiment, when the colorectal cancer protein is to be used to generate antibodies, for example for immunotherapy, the colorectal cancer protein should share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller colorectal cancer protein will be able to bind to the full length protein. In a preferred embodiment, the epitope is unique; that is, antibodies generated to a unique epitope show little or no cross-reactivity.

In one embodiment, the term "antibody" includes antibody fragments, as are known in the art, including Fab, $Fab_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include CGA7 or CJA8, or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include CGA7 or CJA8 polypeptide, or a fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens. In the present case, one of the binding specificities is for the CGA7or CJA8, or a fragment thereof, the other one is for any other antigen, and preferably for a cell-surface protein or receptor or receptor subunit, preferably one that is tumor specific.

In a preferred embodiment, the antibodies to colorectal cancer are capable of reducing or eliminating the biological function of colorectal cancer, as is described below. That is, the addition of anti-colorectal cancer antibodies (either polyclonal or preferably monoclonal) to colorectal cancer (or cells containing colorectal cancer) may reduce or eliminate the colorectal cancer activity. Generally, at least a 25% decrease in activity is preferred, with at least about 50% being particularly preferred and about a 95–100% decrease being especially preferred.

In a preferred embodiment the antibodies to the colorectal cancer proteins are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 15 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1): 86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

By immunotherapy is meant treatment of colorectal cancer with an antibody raised against colorectal cancer proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

In a preferred embodiment the colorectal cancer proteins against which antibodies are raised are secreted proteins as described above. Without being bound by theory, antibodies used for treatment, bind and prevent the secreted protein from binding to its receptor, thereby inactivating the secreted colorectal cancer protein.

In another preferred embodiment, the colorectal cancer protein to which antibodies are raised is a transmembrane protein. Without being bound by theory, antibodies used for treatment, bind the extracellular domain of the colorectal cancer protein and prevent it from binding to other proteins, such as circulating ligands or cell-associated molecules. The antibody may cause down-regulation of the transmembrane colorectal cancer protein. As will be appreciated by one of ordinary skill in the art, the antibody may be a competitive, non-competitive or uncompetitive inhibitor of protein binding to the extracellular domain of the colorectal cancer protein. The antibody is also an antagonist of the colorectal cancer protein. Further, the antibody prevents activation of the transmembrane colorectal cancer protein. In one aspect, when the antibody prevents the binding of other molecules to the colorectal cancer protein, the antibody prevents growth of the cell. The antibody also sensitizes the cell to cytotoxic agents, including, but not limited to TNF-$\alpha$, TNF-$\beta$, IL-1, INF-$\gamma$ and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity. Thus, colorectal cancer is treated by administering to a patient antibodies directed against the transmembrane colorectal cancer protein.

In another preferred embodiment, the antibody is conjugated to a therapeutic moiety. In one aspect the therapeutic moiety is a small molecule that modulates the activity of the colorectal cancer protein. In another aspect the therapeutic moiety modulates the activity of molecules associated with or in close proximity to the colorectal cancer protein. The therapeutic moiety may inhibit enzymatic activity such as protease or protein kinase activity associated with colorectal cancer.

In a preferred embodiment, the therapeutic moiety may also be a cytotoxic agent. In this method, targeting the cytotoxic agent to tumor tissue or cells, results in a reduction in the number of afflicted cells, thereby reducing symptoms associated with colorectal cancer. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against colorectal cancer proteins, or binding of a radionuclide to a chelating agent that has been covalently attached to the antibody. Targeting the therapeutic moiety to transmembrane colorectal cancer proteins not only serves to increase the local concentration of therapeutic moiety in the colorectal cancer afflicted area, but also serves to reduce deleterious side effects that may be associated with the therapeutic moiety.

In another preferred embodiment, the PC protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the PC protein can be targeted within a cell, i.e., the nucleus, an antibody thereto contains a signal for that target localization, i.e., a nuclear localization signal.

The colorectal cancer antibodies of the invention specifically bind to colorectal cancer proteins. By "specifically bind" herein is meant that the antibodies bind to the protein with a binding constant in the range of at least $10^{-4}$–$10^{-6}$ $M^1$, with a preferred range being $10^{-7}$–$10^{-9}$ $M^{-1}$.

In a preferred embodiment, the colorectal cancer protein is purified or isolated after expression. Colorectal cancer proteins-may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the colorectal cancer protein may be purified using a standard anti-colorectal cancer antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the colorectal cancer protein. In some instances no purification will be necessary.

Once expressed and purified if necessary, the colorectal cancer proteins and nucleic acids are useful in a number of applications.

In one aspect, the expression levels of genes are determined for different cellular states in the colorectal cancer phenotype; that is, the expression levels of genes in normal colon tissue and in colorectal cancer tissue (and in some cases, for varying severities of colorectal cancer that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or colorectal cancer tissue.

"Differential expression," or grammatical equivalents as used herein, refers to both qualitative as well as quantitative differences in the genes' temporal and/or cellular expression patterns within and among the cells. Thus, a colorectal cancer gene can qualitatively have its expression altered, including an activation or inactivation, in, for example, normal versus colorectal cancer tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675–1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the colorectal cancer protein and standard immunoassays (ELISAs, etc.) or other techniques, including mass spectroscopy assays, 2D gel electrophoresis assays, etc. Thus, the proteins corresponding to colorectal cancer genes, i.e. those identified as being important in a colorectal cancer phenotype, can be evaluated in a colorectal cancer diagnostic test.

In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the colorectal cancer nucleic acid probes are attached to biochips as outlined herein for the detection and quantification of colorectal cancer sequences in a particular cell. The assays are further described below in the example.

In a preferred embodiment nucleic acids encoding the colorectal cancer protein are detected. Although DNA or RNA encoding the colorectal cancer protein may be detected, of particular interest are methods wherein the mRNA encoding a colorectal cancer protein is detected. The presence of mRNA in a sample is an indication that the colorectal cancer gene has been transcribed to form the mRNA, and suggests that the protein is expressed. Probes to detect the mRNA can be any nucteotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a colorectal cancer protein is detected by binding the digoxygenin with an anti-digoxygenin secondary antibody and developed with nitro blue tetrazolium and 5-bromo4-chloro-3-indoyl phosphate.

In a preferred embodiment, any of the three classes of proteins as described herein (secreted, transmembrane or intracellular proteins) are used in diagnostic assays. The colorectal cancer proteins, antibodies, nucleic acids, modified proteins and cells containing colorectal cancer sequences are used in diagnostic assays. This can be done on an individual gene or corresponding polypeptide level. In a preferred embodiment, the expression profiles are used, preferably in conjunction with high throughput screening techniques to allow monitoring for expression profile genes and/or corresponding polypeptides.

As described and defined herein, colorectal cancer proteins, including intracellular, transmembrane or secreted proteins, find use as markers of colorectal cancer. Detection of these proteins in putative colorectal cancer tissue of patients allows for a determination or diagnosis of colorectal cancer. Numerous methods known to those of ordinary skill in the art find use in detecting colorectal cancer. In one embodiment, antibodies are used to detect colorectal cancer proteins. A preferred method separates proteins from a sample or patient by electrophoresis on a gel (typically a denaturing and reducing protein gel, but may be any other type of gel including isoelectric focusing gels and the like). Following separation of proteins, the colorectal cancer protein is detected by immunoblotting with antibodies raised against the colorectal cancer protein. Methods of immunoblotting are well known to those of ordinary skill in the art.

In another preferred method, antibodies to the colorectal cancer protein find use in in situ imaging techniques. In this method cells are contacted with from one to many antibodies to the colorectal cancer protein(s). Following washing to remove non-specific antibody binding, the presence of the antibody or antibodies is detected. In one embodiment the antibody is detected by incubating with a secondary antibody that contains a detectable label. In another method the primary antibody to the colorectal cancer protein(s) contains a detectable label. In another preferred embodiment each one of multiple primary antibodies contains a distinct and detectable label. This method finds particular use in simultaneous screening for a pluralilty of colorectal cancer proteins. As will be appreciated by one of ordinary skill in the art, numerous other histological imaging techniques are useful in the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing colorectal cancer from blood samples and other bodily secretions. As previously described, certain colorectal cancer proteins are secreted/circulating molecules. Blood samples and other bodily secretions, including, but not limited to, saliva, mucous, tears, sweat, sebacious oils, urine, feces, bile, lymph, cerebrospinal fluid, etc., therefore, are useful as samples to be probed or tested for the presence of secreted colorectal cancer proteins. Antibodies can be used to detect the colorectal cancer by any of the previously described immunoassay techniques including ELISA, immunoblotting (Western blotting), immunoprecipitation, BIACORE technology and the like, as will be appreciated by one of ordinary skill in the art.

In a preferred embodiment, in situ hybridization of labeled colorectal cancer nucleic acid probes to tissue arrays is done. For example, arrays of tissue samples, including colorectal cancer tissue and/or normal tissue, are made. In situ hybridization as is known in the art can then be done.

It is understood that when comparing the fingerprints between an individual and a standard, the skilled artisan can make a diagnosis as well as a prognosis. It is further understood that the genes which indicate the diagnosis may differ from those which indicate the prognosis.

In a preferred embodiment, the colorectal cancer proteins, antibodies, nucleic acids, modified proteins and cells containing colorectal cancer sequences are used in prognosis assays. As above, gene expression profiles can be generated that correlate to colorectal cancer severity, in terms of long term prognosis. Again, this may be done on either a protein or gene level, with the use of genes being preferred. As above, the colorectal cancer probes are attached to biochips for the detection and quantification of colorectal cancer sequences in a tissue or patient. The assays proceed as outlined for diagnosis.

In a preferred embodiment, any of the three classes of proteins as described herein are used in drug screening assays. The colorectal cancer proteins, antibodies, nucleic acids, modified proteins and cells containing colorectal cancer sequences are used in drug screening assays or by evaluating the effect of drug candidates on a "gene expression profile" or expression profile of polypeptides. In a preferred embodiment, the expression profiles are used, preferably in conjunction with high throughput screening techniques to allow monitoring for expression profile genes after treatment with a candidate agent, Zlokarnik, et al., Science 279, 84–8 (1998), Heid, 1996 #69.

In a preferred embodiment, the colorectal cancer proteins, antibodies, nucleic acids, modified proteins and cells containing the native or modified colorectal cancer proteins are used in screening assays. That is, the present invention provides novel methods for screening for compositions which modulate the colorectal cancer phenotype. As above, this can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Having identified the colorectal cancer genes herein, a variety of assays may be executed. In a preferred embodiment, assays may be run on an individual gene or protein level. That is, having identified a particular gene as up regulated in colorectal cancer, candidate bioactive agents may be screened to modulate this gene's response; preferably to down regulate the gene, although in some circumstances to up regulate the gene. "Modulation" thus includes both an increase and a decrease in gene expression. The preferred amount of modulation will depend on the original change of the gene expression in normal versus tumor tissue, with changes of at least 10%, preferably 50%, more preferably 100–300%, and in some embodiments 300–1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired.

As will be appreciated by those in the art, this may be done by evaluation at either the gene or the protein level; that is, the amount of gene expression may be monitored using nucleic acid probes and the quantification of gene expression levels, or, alternatively, the gene product itself can be monitored, for example through the use of antibodies to the colorectal cancer protein and standard immunoassays.

In a preferred embodiment, gene expression monitoring is done and a number of genes, i.e. an expression profile, is monitored simultaneously, although multiple protein expression monitoring can be done as well.

In this embodiment, the colorectal cancer nucleic acid probes are attached to biochips as outlined herein for the detection and quantification of colorectal cancer sequences in a particular cell. The assays are further described below.

Generally, in a preferred embodiment, a candidate bioactive agent is added to the cells prior to analysis. Moreover, screens are provided to identify a candidate bioactive agent which modulates colorectal cancer, modulates colorectal cancer proteins, binds to a colorectal cancer protein, or interferes between the binding of a colorectal cancer protein and an antibody.

The term "candidate bioactive agent" or "drug candidate" or grammatical equivalents as used herein describes any molecule, e.g., protein, oligopeptide, small organic molecule, polysaccharide, polynucleotide, etc., to be tested for bioactive agents that are capable of directly or indirectly altering the colorectal cancer phenotype or the expression of a colorectal cancer sequence, including both nucleic acid sequences and protein sequences. In preferred embodiments, the bioactive agents modulate the expression profiles, or expression profile nucleic acids or proteins provided herein. In a particularly preferred embodiment, the candidate agent suppresses a colorectal cancer phenotype, for example to a normal colon tissue fingerprint. Similarly, the candidate agent preferably suppresses a severe colorectal cancer phenotype. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of a CRC protein. By "neutralize" is meant that activity of a protein is either inhibited or counter acted against so as to have substantially no effect on a cell.

Candidate agents encompass numerous chemical classes, though typically they are organic molecules, preferably small organic compounds having a molecular weight of more than 100 and less than about 2,500 daltons (D). Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If nonnaturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

After the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with biotin-FITC or PE, or with cy3 or cy5.

In a preferred embodiment, the target sequence is labeled with, for example, a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the assay is run, the data is analyzed to determine the expression levels, and changes in expression levels as between states, of individual genes, forming a gene expression profile.

The screens are done to identify drugs or bioactive agents that modulate the colorectal cancer phenotype. Specifically, there are several types of screens that can be run. A preferred embodiment is in the screening of candidate agents that can induce or suppress a particular expression profile, thus preferably generating the associated phenotype. That is, candidate agents that can mimic or produce an expression profile in colorectal cancer similar to the expression profile of normal colon tissue is expected to result in a suppression of the colorectal cancer phenotype. Thus, in this embodiment, mimicking an expression profile, or changing one profile to another, is the goal.

In a preferred embodiment, as for the diagnosis and prognosis applications, having identified the colorectal cancer genes important in any one state, screens can be run to alter the expression of the genes individually. That is, screening for modulation of regulation of expression of a single gene can be done; that is, rather than try to mimic all or part of an expression profile, screening for regulation of individual genes can be done. Thus, for example, particularly in the case of target genes whose presence or absence is unique between two states, screening is done for modulators of the target gene expression.

In a preferred embodiment, screening is done to alter the biological function of the expression product of the colorectal cancer gene. Again, having identified the importance of a gene in a particular state, screening for agents that bind and/or modulate the biological activity of the gene product can be run as is more fully outlined below.

Thus, screening of candidate agents that modulate the colorectal cancer phenotype either at the gene expression level or the protein level can be done.

In addition screens can be done for novel genes that are induced in response to a candidate agent. After identifying a candidate agent based upon its ability to suppress a colorectal cancer expression pattern leading to a normal expression pattern, or modulate a single colorectal cancer gene expression profile so as to mimic the expression of the gene from normal tissue, a screen as described above can be performed to identify genes that are specifically modulated in response to the agent. Comparing expression profiles between normal tissue and agent treated colorectal cancer tissue reveals genes that are not expressed in normal colon tissue or colorectal cancer tissue, but are expressed in agent treated tissue. These agent specific sequences can be identified and used by any of the methods described herein for colorectal cancer genes or proteins. In particular these sequences and the proteins they encode find use in marking or identifying agent treated cells. In addition, antibodies can be raised against the agent induced proteins and used to target novel therapeutics to the treated colorectal cancer tissue sample.

Thus, in one embodiment, a candidate agent is administered to a population of colorectal cancer cells, that thus has an associated colorectal cancer expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, colorectal cancer tissue may be screened for agents that reduce or suppress the colorectal cancer phenotype. A change in at least one gene of the expression profile indicates that the agent has an effect on colorectal cancer activity. By defining such a signature for the colorectal cancer phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular colorectal cancer gene as important in a particular state, screening of modulators of either the expression of the gene or the gene product itself can be done. The gene products of colorectal cancer genes are sometimes referred to herein as "colorectal cancer proteins" or "colorectal cancer modulating proteins" or "CCMP". Additionally, "modulator" and "modulating" proteins are sometimes used interchangeably herein. In one embodiment, the colorectal cancer protein is termed CGA7. In another embodiment, the colorectal cancer protein is termed CJA8. CGA7 or CJA8 sequences can be identified as described herein for colorectal cancer sequences. In one embodiment, a CGA7 protein sequence comprises the sequence depicted in FIG. 2 (SEQ ID NO: 2). In a preferred embodiment, a CGA7 protein sequence has the sequence depicted in FIG. 4 (SEQ ID NO: 4). In another embodiment, a CJA8 protein sequence comprises the sequence depicted in FIG. 6 (SEQ ID NO: 6). In a preferred embodiment, a CJA8 protein sequence has the sequence depicted in FIG. 8 (SEQ ID NO: 8). The colorectal cancer protein may be a fragment, or alternatively, be the full length protein to the fragment shown herein. Preferably, the colorectal cancer protein is a fragment. In a preferred embodiment, the amino acid sequence which is used to determine sequence identity or similarity is that depicted in FIG. 4 (SEQ ID NO: 4). In another preferred embodiment, the amino acid sequence which is used to determine sequence identity or similarity is that depicted in FIG. 8 (SEQ ID NO: 8). In another embodiment, the sequences are naturally occurring allelic variants of a protein having the sequence depicted in FIG. 4 (SEQ ID NO: 4). In yet another embodiment, the sequences are naturally occurring allelic variants of a protein having the sequence depicted in FIG. 8 (SEQ ID NO: 8). In another embodiment, the sequences are sequence variants as further described herein.

Preferably, the colorectal cancer protein is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the c-terminus of the fragment is kept as a free acid and the n-terminus is a free amine to aid in coupling, i.e., to cysteine. Preferably, the fragment of approximately 14 to 24 amino acids long. More preferably the fragment is a soluble fragment. In one embodiment, a CGA7 fragment has at least one CGA7 bioactivity as defined below. In another embodiment, a CJA8 fragment has at least one CJA8 bioactivity as defined below.

In a preferred embodiment, the colorectal cancer protein fragment is as depicted in FIG. 4 (SEQ ID NO: 4). In another preferred embodiment, the colorectal cancer protein fragment is as depicted in FIG. 8 (SEQ ID NO: 8).

In one embodiment the colorectal cancer proteins are conjugated to an immunogenic agent as discussed herein. In one embodiment the colorectal cancer protein is conjugated to BSA.

Thus, in a preferred embodiment, screening for modulators of expression of specific genes can be done. This will be done as outlined above, but in general the expression of only one or a few genes are evaluated.

In a preferred embodiment, screens are designed to first find candidate agents that can bind to colorectal cancer proteins, and then these agents may be used in assays that evaluate the ability of the candidate agent to modulate colorectal cancer activity. Thus, as will be appreciated by those in the art, there are a number of different assays which may be run; binding assays and activity assays.

In a preferred embodiment, binding assays are done. In general, purified or isolated gene product is used; that is, the gene products of one or more colorectal cancer nucleic acids are made. In general, this is done as is known in the art. For example, antibodies are generated to the protein gene products, and standard immunoassays are run to determine the amount of protein present. Alternatively, cells comprising the colorectal cancer proteins can be used in the assays.

Thus, in a preferred embodiment, the methods comprise combining a colorectal cancer protein and a candidate bioactive agent, and determining the binding of the candidate agent to the colorectal cancer protein. Preferred embodiments utilize the human colorectal cancer protein, although other mammalian proteins may also be used, for example for the development of animal models of human disease. In some embodiments, as outlined herein, variant or derivative colorectal cancer proteins may be used.

Generally, in a preferred embodiment of the methods herein, the colorectal cancer protein or the candidate agent is non-diffusably bound to an insoluble support having isolated sample receiving areas (e.g. a microtiter plate, an array, etc.). It is understood that alternatively, soluble assays known in the art may be performed. The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the colorectal cancer protein is bound to the support, and a candidate bioactive agent is added to the assay. Alternatively, the candidate agent is bound to the support and the colorectal cancer protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein—protein binding assays, electrophoretic mobility shift assays, immunoassays for protein binding, functional assays (phosphorylation assays, etc.) and the like.

The determination of the binding of the candidate bioactive agent to the colorectal cancer protein may be done in a number of ways. In a preferred embodiment, the candidate bioactive agent is labelled, and binding determined directly. For example, this may be done by attaching all or a portion of the colorectal cancer protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. colorectal cancer), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the colorectal cancer protein and thus is capable of binding to, and potentially modulating, the activity of the colorectal cancer protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the colorectal cancer protein with a higher affinity. Thus, if the candidate bioactive agent is labeled, the presence of the label on the support, coupled with a lack of competitor binding, may indicate that the candidate agent is capable of binding to the colorectal cancer protein.

In a preferred embodiment, the methods comprise differential screening to identity bioactive agents that are capable of modulating the activity of the colorectal cancer proteins. In this embodiment, the methods comprise combining a colorectal cancer protein and a competitor in a first sample. A second sample comprises a candidate bioactive agent, a colorectal cancer protein and a competitor. The binding of the competitor is determined for both samples, and a change, or difference in binding between the two samples indicates the presence of an agent capable of binding to the colorectal cancer protein and potentially modulating its activity. That is, if the binding of the competitor is different in the second sample relative to the first sample, the agent is capable of binding to the colorectal cancer protein.

Alternatively, a preferred embodiment utilizes differential screening to identify drug candidates that bind to the native colorectal cancer protein, but cannot bind to modified colorectal cancer proteins. The structure of the colorectal cancer protein may be modeled, and used in rational drug design to synthesize agents that interact with that site. Drug candidates that affect colorectal cancer bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein—protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of colorectal cancer proteins may also be done. In a preferred embodiment, methods for screening for a bioactive agent capable of modulating the activity of colorectal cancer proteins comprise the steps of adding a candidate bioactive agent to a sample of colorectal cancer proteins, as above, and determining an alteration in the biological activity of colorectal cancer proteins. "Modulating the activity" of colorectal cancer includes an increase in activity, a decrease in activity, or a change in the type or kind of activity present. Thus, in this embodiment, the candidate agent should both bind to colorectal cancer proteins (although this may not be necessary), and alter its biological or biochemical activity as defined herein. The methods include both in vitro screening methods, as are generally outlined above, and in vivo screening of cells for alterations in the presence, distribution, activity or amount of colorectal cancer proteins.

Thus, in this embodiment, the methods comprise combining a colorectal cancer sample and a candidate bioactive agent, and evaluating the effect on colorectal cancer activity. By "colorectal cancer activity" or grammatical equivalents herein is meant at least one of colorectal cancer's biological activities, including, but not limited to, cell division, preferably in colon tissue, cell proliferation, tumor growth, transformation of cells and serine protease activity. In one embodiment, colorectal cancer activity includes activation of CGA7 or a substrate thereof by CGA7. In another embodiment, colorectal cancer activity includes activation of CJA8 or a substrate thereof by CJA8. An inhibitor of colorectal cancer activity is an agent which inhibits any one or more colorectal cancer activities.

In a preferred embodiment, the activity of the colorectal cancer protein is increased; in another preferred embodiment, the activity of the colorectal cancer protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a colorectal cancer protein. The methods comprise adding a candidate bioactive agent, as defined above, to a cell comprising colorectal cancer proteins. Preferred cell types include almost any cell. The cells contain a recombinant nucleic acid that encodes a colorectal cancer protein. In a preferred embodiment, a library of candidate agents are tested on a plurality of cells.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell—cell contacts). In another example, the determinations are determined at different stages of the cell cycle process.

In this way, bioactive agents are identified. Compounds with pharmacological activity are able to enhance or interfere with the activity of the colorectal cancer protein. In one embodiment, "colorectal cancer protein activity", "colorectal cancer protein bioactivity" and grammatical equivalents thereof as used herein includes at least one of the following:

colorectal cancer activity, binding to CGA7, binding to CJA8, activation of CGA7, activation of CJA8, activation of substrates of CGA7 by CGA7, or activation of substrates of CJA8 by CJA8. An inhibitor of CGA7 inhibits at least one of CGA7's bioactivities. An inhibitor of CJA8 inhibits at least one of CJA8's bioactivities.

In one embodiment, a method of inhibiting colorectal cancer cell division is provided. The method comprises administration of a colorectal cancer inhibitor.

In another embodiment, a method of inhibiting colorectal tumor growth is provided. The method comprises administration of a colorectal cancer inhibitor. In a preferred embodiment, the inhibitor is an inhibitor of CGA7. In another preferred embodiment, the inhibitor is an inhibitor of CJA8.

In a further embodiment, methods of treating cells or individuals with colorectal cancer are provided. The method comprises administration of a colorectal cancer inhibitor. In a preferred embodiment, the inhibitor is an inhibitor of CGA7. In another preferred embodiment, the inhibitor is an inhibitor of CJA8. In one embodiment, a colorectal cancer inhibitor is an antibody as discussed above. In another embodiment, the colorectal cancer inhibitor is an antisense molecule. Antisense molecules as used herein include antisense or sense oligonucleotides comprising a singe-stranded nucleic acid sequence (either RNA or DNA) capable of binding to target mRNA (sense) or DNA (antisense) sequences for colorectal cancer molecules. A preferred antisense molecule is for CGA7 or for a ligand or activator thereof. Another preferred antisense molecule is for CJA8 or for a ligand or activator thereof. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %. The agents may be administered alone or in combination with other treatments, i.e., radiation.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the various colorectal cancer sequences are important in colorectal cancer. Accordingly, disorders based on mutant or variant colorectal cancer genes may be determined. In one embodiment, the invention provides methods for identifying cells containing variant colorectal cancer genes comprising determining all or part of the sequence of at least one endogenous colorectal cancer gene in a cell. As will be appreciated by those in the art, this may be done using any number of sequencing techniques. In a preferred embodiment, the invention provides methods of identifying the colorectal cancer genotype of an individual comprising determining all or part of the sequence of at least one colorectal cancer gene of the individual. This is generally done in at least one tissue of the individual, and may include the evaluation of a number of tissues or different samples of the same tissue. The method may include comparing the sequence of the sequenced gene to a known gene, i.e. a wild-type gene.

The sequence of all or part of the colorectal cancer gene can then be compared to the sequence of a known colorectal cancer gene to determine if any differences exist. This can be done using any number of known homology programs, such as Bestfit, etc. In a preferred embodiment, the presence of a difference in the sequence between the colorectal cancer gene of the patient and the known colorectal cancer gene is indicative of a disease state or a propensity for a disease state, as outlined herein.

In a preferred embodiment, the colorectal cancer genes are used as probes to determine the number of copies of the colorectal cancer gene in the genome.

In another preferred embodiment colorectal cancer genes are used as probed to determine the chromosomal localization of the colorectal cancer genes. Information such as chromosomal localization finds use in providing a diagnosis or prognosis in particular when chromosomal abnormalities such as translocations, and the like are identified in colorectal cancer gene loci.

Thus, in one embodiment, methods of modulating colorectal cancer in cells or organisms are provided. In one embodiment, the methods comprise administering to a cell an antibody that reduces or eliminates the biological activity of an endogenous colorectal cancer protein. Alternatively, the methods comprise administering to a cell or organism a recombinant nucleic acid encoding a colorectal cancer protein. As will be appreciated by those in the art, this may be accomplished in any number of ways. In a preferred embodiment, for example when the colorectal cancer sequence is down-regulated in colorectal cancer, the activity of the colorectal cancer gene is increased by increasing the amount in the cell, for example by overexpressing the endogenous colorectal cancer protein or by administering a gene encoding the colorectal cancer sequence, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, for example when the colorectal cancer sequence is up-regulated in colorectal cancer, the activity of the endogeneous gene is decreased, for example by the administration of an inhibitor of colorectal cancer, such as an antisense nucleic acid.

In one embodiment, the colorectal cancer proteins of the present invention may be used to generate polyclonal and monoclonal antibodies to colorectal cancer proteins, which are useful as described herein. Similarly, the colorectal cancer proteins can be coupled, using standard technology, to affinity chromatography columns. These columns may then be used to purify colorectal cancer antibodies. In a preferred embodiment, the antibodies are generated to epitopes unique to a colorectal cancer protein; that is, the antibodies show little or no cross-reactivity to other proteins. These antibodies find use in a number of applications. For example, the colorectal cancer antibodies may be coupled to standard affinity chromatography columns and used to purify colorectal cancer proteins. The antibodies may also be used as blocking polypeptides, as outlined above, since they will specifically bind to the colorectal cancer protein.

In one embodiment, a therapeutically effective dose of a colorectal cancer protein or nucleic acid, or modulator thereof (e.g., an antibody), is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for degradation of the administered protein or nucleic acid, or modulator thereof, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the colorectal cancer proteins, nucleic acids and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the colorectal cancer proteins and modulators may be directly applied as a solution or spray.

The pharmaceutical compositions of the present invention comprise a colorectal cancer protein or nucleic acid, or modulator thereof, in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, colorectal cancer proteins and modulators are administered as therapeutic agents, and can be formulated as outlined above. Similarly, colorectal cancer genes (including both the full-length sequence, partial sequences, or regulatory sequences of the colorectal cancer coding regions) can be administered in gene therapy applications, as is known in the art. These colorectal cancer genes can include antisense applications, either as gene therapy (i.e. for incorporation into the genome) or as antisense compositions, as will be appreciated by those in the art.

In a preferred embodiment, colorectal cancer genes are administered as DNA vaccines, either single genes or combinations of colorectal cancer genes. Naked DNA vaccines are generally known in the art. Brower, Nature Biotechnology, 16:1304–1305 (1998).

In one embodiment, colorectal cancer genes of the present invention are used as DNA vaccines. Methods for the use of genes as DNA vaccines are well known to one of ordinary skill in the art, and include placing a colorectal cancer gene or portion of a colorectal cancer gene under the control of a promoter for expression in a patient with colorectal cancer. The colorectal cancer gene used for DNA vaccines can encode full-length colorectal cancer proteins, but more preferably encodes portions of the colorectal cancer proteins including peptides derived from the colorectal cancer protein. In a preferred embodiment a patient is immunized with a DNA vaccine comprising a plurality of nucleotide sequences derived from a colorectal cancer gene. Similarly, it is possible to immunize a patient with a plurality of colorectal cancer genes or portions thereof as defined herein. Without being bound by theory, expression of the polypeptide encoded by the DNA vaccine, cytotoxic T-cells, helper T-cells and antibodies are induced which recognize and destroy or eliminate cells expressing colorectal cancer proteins.

In a preferred embodiment, the DNA vaccines include a gene encoding an adjuvant molecule with the DNA vaccine. Such adjuvant molecules include cytokines that increase the immunogenic response to the colorectal cancer polypeptide encoded by the DNA vaccine. Additional or alternative adjuvants are known to those of ordinary skill in the art and find use in the invention.

In another preferred embodiment colorectal cancer genes find use in generating animal models of colorectal cancer. For example, as is appreciated by one of ordinary skill in the art, when the colorectal cancer gene identified is repressed or diminished in colorectal cancer tissue, gene therapy technology wherein antisense RNA directed to the colorectal cancer gene will also diminish or repress expression of the gene. An animal generated as such serves as an animal model of colorectal cancer that finds use in screening bioactive drug candidates. Similarly, gene knockout technology, for example as a result of homologous recombination with an appropriate gene targeting vector, will result in the absence of the colorectal cancer protein. When desired, tissue-specific knockout of the colorectal cancer protein may be necessary.

It is also possible that the colorectal cancer protein is overexpressed in colorectal cancer. As such, transgenic animals can be generated that overexpress the colorectal cancer protein. Similarly, animals can be generated that express a fragment or a mutant of the colorectal cancer protein. Depending on the desired expression level, promoters of various strengths can be employed to express the transgene. Tissue-specific expression may also be obtained using selected promoters. In addition, the number of copies of the integrated transgene can be determined and compared for a determination of the expression level of the transgene.

In another aspect, animal models may be developed using cell lines. Cell lines which overexpress a colorectal cancer protein as compared with normal tissue can be identified. Such cell lines may be implanted in an animal to model a tumor. Such cell grafts may be used to determine the targeting of a candidate agent to a specific colorectal cancer protein or the efficacy of a candidate agent upon administration to an animal.

Animals such as those described above find use as animal models of colorectal cancer and are additionally useful in screening for bioactive molecules to treat disorders related to the colorectal cancer protein.

It is understood that the examples described herein in no way serve to limit the true scope of this invention, but rather are presented for illustrative purposes. All references and sequences of accession numbers cited herein are incorporated by reference in their entirety.

EXAMPLES

Example 1

Hybridization of cRNA to oligonucleotide arrays

This protocol outlines the method for purification and labeling of RNA for hybridization to oligonucleotide arrays. Total RNA is purified from cells or tissue, double-stranded cDNA is prepared from the RNA, the cDNA is purified, the cDNA is then labeled with biotin during an in vitro transcription (IVT) reaction, the cRNA prepared in the IVT reaction is purified, fragmented, and hybridized to an oligonucleotide array.

Purification of Total RNA from Tissue or Cells

Homogenization

Before using the tissue homogenizer (Polytron PT3100 fitted with probe 9100072, Kinematica), clean it with soapy water and rinse thoroughly. Sterilize by running the homogenizer in ethanol, and then run the homogenizer in at least 3 mL of TRIzol reagent (Life Technology/GibcoBRL).

Estimate tissue weight. Homogenize tissue samples in 1 mL of TRizol per 50 mg of tissue. If cells derived from experimental model systems are used as the source of RNA, use 1 mL of TRIzol per 5–10×106 cells. Homogenize tissue or cells thoroughly.

After each sample homogenization run the probe in at least 3 mL fresh TRIzol, and then add this TRIzol back to the homogenized sample. Wash the probe with at least 50 mL fresh RNase-free water before proceeding to the next sample.

RNA isolation

Following sample homogenization, centrifuge sample in a microfuge at 12 OOOg for 10 min at 4° C. (microfuge tubes) or in a Sorvall centrifuge (Sorvall Centrifuge RT7 Plus) at 4000 RPM for 60 min at 4° C. (15 mL conical tubes).

Transfer 1 mL of supernatant to a new microcentrifuge tube. Add 0.5 uL linear acrylamide and incubate at room temperature for 4 minutes. Store the remaining clarified homogenate at −20° C. or colder. Add 0.2 mL chloroform. Invert tube and shake vigorously for 15 seconds until sample is thoroughly mixed. Inclubate sample at room temperature for 5 minutes. Centrifuge at 12 OOOg for 15 minutes at 4° C.

Transfer aqueous (top clear) layer to a new microcentrifuge tube, being careful not to remove any of the material at the aqueous/organic phase interface. Add 0.5 mL isopropanol, vortex for 2 seconds, and incubate at RT for 10 minutes. Centrifuge at 10 OOOg for 10 minutes at 4° C.

Pour off supernatant, add 1 mL cold 75% ethanol, invert tube to loosen pellet, and centrifuge at 750 Og for 5 min at 4° C.

Pour off supernatant, spin in microcentrifuge briefly and use a pipette to remove the remaining ethanol wash from the pellet. Dry the pellet at room temperature in a fume hood for at least 10 minutes.

Resuspend RNA pellet in 50 uL RNase-free water. Vortex. Incubate at 65° C. for 10 minutes, vortex for 3 seconds to resuspend pellet, and spin briefly to collect sample in the bottom of the microcentrifuge tube.

RNA Quantification and Quality Control

Use 1 uL of RNA sample to quantify RNA in a spectrometer. The ratio of the optical density readings at 260 and 280 nm should be between 1.4 and 2.0 OD. Use between 250–500 ng of RNA sample to run on a 1% agarose electrophoretic gel to check integrity of 28 S, 18 S and 5 S RNAs. Smearing of the RNA should be minimal and not biased toward RNAs of lower molecular weight.

RNA Purification

Purify no more than 100 ug of RNA on an individual RNeasy column (Qiagen). Follow manufacturer's instructions for RNA purification. Adjust the sample to a volume of 100 uL with RNase-free water. Add 350 uL Buffer RLT and then 250 uL ethanol to the sample. Mix gently by pipetting and then apply sample to the RNeasy column. Centrifuge in a microcentrifuge for 15 seconds at 10000 RPM.

Transfer column to a new 2 mL collection tube. Add 500 uL Buffer RPE and centrifuge again for 15 seconds at 10000 RPM.

Discard flow through. Add 500 uL Buffer RPE and centrifuge for 15 seconds at 10000 RPM.

Discard flow through. Centrifuge for 2 minutes at 15 000 RPM to dry column.

Transfer column to a new 1.5 mL collection tube and apply 30–40 uL of RNase-free water directly onto the column membrane. Let the column sit for 1 minute, then centrifuge at 10 000 RPM. Repeat the elusion with another 30–40 uL RNase-free water. Store RNA at −20° C. or colder.

Preparation of polyA+ RNA

PolyA+ RNA can be purified from total RNA if desired using the Oligotex mRNA Purification System (Qiagen) by following the manufacturer's instructions. Before proceeding with cDNA synthesis the polyA+ RNA must be ethanol precipitated and resuspended as the Oligotex procedure leaves a reagent in the polyA+ RNA which inhibits downstream reactions.

cDNA Synthesis

Reagents for cDNA synthesis are obtained from the SuperScript Choice System for cDNA Synthesis kit (GibcoBRL).

Before aliquoting RNA to use in cDNA synthesis, heat RNA at 70° C. for 2 minutes to dislodge RNA that is adhering to the plastic tube. Vortex, spin briefly in microcentrifuge, and then keep RNA at room temperature until aliquot is taken.

Use 5–10 ug of total RNA or 1 ug of polyA+ RNA as starting material.

Combine Primers and RNA

| Total RNA | 5–10 ug |
|---|---|
| T7-(dT)$_{24}$ primer (100 pmol/uL) | 1 uL (2 ug/uL) |
| Add water to a total volume of | 11 uL |
| Heat to 70° C. for 10 minutes. Place on ice for 2 minutes. | |

First Strand Synthesis Reaction

Add 7 μL of the following first strand reaction mix to each RNA-primer sample:

| 5X First strand buffer | 4 uL (Final concentration: 1X) |
|---|---|
| 0.1 M DTT | 2 uL (Final concentration: 0.01 M) |
| 10 mM dNTPs | 1 uL (Final concentration: 0.5 mM) |
| Incubate sample at 37° C. for 2 minutes. | |
| To each sample add: | |
| Superscript II reverse transcriptase | 2 uL |
| Incubate at 37° C. for 1 hour and then place sample on ice. | |

Second Strand cDNA Synthesis Reaction

Prepare the following second strand reaction mix for each sample:

| DEPC water | 91 uL |
|---|---|
| 5X Second strand buffer | 30 uL (Final concentration: 1X) |
| 10 mM dNTPs | 3 uL (Final concentration: 0.2 mM) |
| E. coli DNA ligase (10 U/uL) | 1 uL |
| E. coli DNA Polymerase (10 U/uL) | 4 uL |
| E. coli RNase H (2 U/uL) | 1 uL |

Total volume of second strand reaction mix per sample is 130 u L. Add mix to first strand cDNA synthesis sample.

Incubate 2 hours at 16° C. Add 2 uL T4 DNA Polymerase and incubate 4 minutes at 16° C. Add 10 ul of 0.5 M EDTA to stop the reaction and place the tubes on ice.

Purification of cDNA

Use Phase Lock Gel Light tubes (Eppendorf) for cDNA purification.

Spin Phase Lock Gel tubes for 1 minute at 15 000 RPM. Add the cDNA sample. Add an equal volume of pH 8 phenol:choloform:isoamyl alcohol (25:24:1), shake vigorously and then centrifuge for 5 minutes at 15 000 RPM.

Transfer the upper (aqueous) phase to a new microcentrifuge tube. Ethanol precipitate the DNA by adding 1 volume of 5 M NH4OAc and 2.5 volumes of cold (−20° C.) 100% ethanol. Vortex and then centrifuge at 16° C. for 30 minutes at 15 000 RPM.

Remove supernatant from cDNA pellet and then wash pellet with 500 uL of cold (−20° C.) 80% ethanol. Centrifuge sample for 5 min at 16° C. at 15 000 RPM. Remove the supernatant, repeat 80% ethanol wash once more, remove supernatant, and then allow pellet to air dry. Resuspend pellet in 3 uL of RNase-free water.

In vitro Transcription (IVT) and Labeling with Biotin

In vitro transcription is performed using reagents from the T7 Megascript kit (Ambion) unless otherwise indicated.

Aliquot 1.5 uL of cDNA into an RNase-free thin walled PCR tube and place on ice.

Prepare the following IVT mix at room temperature:

| T7 10XATP (75 mM) | 2 uL |
|---|---|
| T7 10XGTP (75 mM) | 2 uL |
| T7 10XCTP (75 mM) | 1.5 uL |
| T7 10XUTP (75 mM) | 1.5 uL |
| Bio-11-UTP (10 mM) | 3.75 uL (Boehringer Mannheim or Enzo Diagnostics) |
| Bio-16-CTP (10 mM) | 3.75 uL (Enzo Diagnostics) |
| T7 buffer (10X) | 2 uL |
| T7 enzyme mix (10X) | 2 uL |

Remove the cDNA from ice and add 18.5 uL of IVT mix to each cDNA sample. Final volume of sample is 20 uL.

Incubate at 37° C. for 6 hours in a PCR machine, using a heated lid to prevent condensation.

Purification of labeled IVT product

Use RNeasy columns (Qiagen) to purify IVT product. Follow manufacturer's instructions or see section entitled "RNA purification using RNeasy Kit" above.

Elute IVT product two times using 20–30 uL of RNase-free water. Quantitate IVT yield by taking an optical density reading. If the concentration of the sample is less than 0.4 ug/uL, then ethanol precipitate and resuspend in a smaller volume.

Fragmentation of cRNA

Aliquot 15 ug of cRNA in a maximum volume of 16 uL into a microfuge tube. Add 2 uL of 5× Fragmentation buffer for every 8 uL of cRNA used.

5× Fragmentation buffer:
100 mM Tris-acetate, pH 8.1
500 mM potassium acetate
150 mM magnesium acetate Incubate for 35 minutes at 95° C. Centrifuge briefly and place on ice.

Hybridization of cRNA to Olinonucleotide Array

10–15 ug of cRNA are used in a total volume of 300 uL of hybridization solution. Prepare the hybridization solution as follows:

| Fragmented cRNA (15 ug) | 20 uL |
|---|---|
| 948-b control oligonucleotide (Affymetrix) | 50 pM |
| BioB control cRNA (Affymetrix) | 1.5 pM |
| BioC control cRNA (Affymetrix) | 5 pM |
| BioD control cRNA (Aftymetrix) | 25 pM |
| CRE control cRNA (Affymetrix) | 100 pM |
| Herring sperm DNA (10 mg/mL) | 3 uL |
| Bovine serum albumin (50 mg/mL) | 3 uL |
| 2X MES | 150 uL |
| RNase-free water | 118 uL |

Example 2

Hybridization to Oligonucleotide Arrays

This method allows one to compare RNAs from two different sources on the same oligonucleotide array (for example, RNA prepared from tumor tissue versus RNA prepared from normal tissue). The starting material for this method is IVT product prepared as described in Example 1, above. The cRNA is reverse transcribed in the presence of either Cy3 (sample 1) or Cy5 (sample 2) conjugated dUTP. After labeling the two samples, the RNA is degraded and the samples are purified to recover the Cy3 and Cy5 dUTP. The differentially labelled samples are combined and the cDNA is further purified to remove fragments less than 100 bp in length. The sample is then fragmented and hybridized to oligonucleotide arrays.

Labeling of cRNA

Prepare reaction in RNase-free thin-walled PCR tubes. Use non-biotinylated IVT product as prepared above in Example 1. This IVT product can also be prepared from DNA.

| IVT cRNA | 4 ug |
|---|---|
| Random Hexamers (1 ug/uL) | 4 uL |
| Add RNase-free water to a total volume of | 14 uL |
| Incubate at 70° C. for 10 minutes, and then place on ice. | |

Prepare a 50× dNTP mix by combining NTPs obtained from Amersham Pharmacia Biotech:

| 100 mM dATP | 25 uL (Final concentration: 25 mM) |
|---|---|
| 100 mM dCTP | 25 uL (Final concentration: 25 mM) |
| 100 mM dGTP | 25 uL (Final concentration: 25 mM) |
| 100 mM dTTP | 10 uL (Final concentration: 10 mM) |
| RNase-free water | 15 uL |

Reverse transcription is performed on the IVT product by adding the following reagents from the SuperScript Choice System for cDNA Synthesis kit (GibcoBRL) to the IVT-random hexamer mixture.

| 5X first strand buffer | 6 uL |
|---|---|
| 0.1 MDTT | 3 uL |
| 50X dNTP mix | 0.6 uL (as prepared above) |
| RNase-free water | 2.4 uL |
| Cy3 or Cy5 dUTP (1 mM) | 3 uL (Amersham Pharmacia Biotech) |
| SuperScript II reverse transcriptase | 1 uL |

Incubate for 30 minutes at 42° C.

Add 1 uL SuperScript iI reverse transcriptase and let reaction proceed for 1 hour at 42° C. Place reaction on ice.

RNA degradation

Prepare degradation buffer composed of 1 M NaOH and 2 mM EDTA. To the labeled cDNA mixture above, add:

Degradation buffer 1.5 uL

Incubate at 65° C. for 10 minutes.

Recovery of CY3 and Cv5-dUTP

Combine each sample with 500 uL TE and apply onto a Microcon 30 column. Spin column at 10 000 RPM in a microcentrifuge for 10 minutes. Recycle Cy3 and Cy5 dUTP contained in column flow-through. Proceed with protocol using concentrated sample remaining in column.

Purification of cDNA cDNA is purified using the Qiaquick PCR Purification Kit (Qiagen), following the manufacturer's directions.

Combine the Cy3 and Cy5 labelled samples that are to be compared on the same chip. Add:

| 3M NaOAc | 2 uL |
|---|---|
| Buffer PB | 5 volumes |

Apply sample to Qiaquick column. Spin at 10 00 Og in a microcentrifuge for 10 minutes Discard flow through and add 750 uL Buffer PB to column. Centrifuge at 10 00 Og for 1 minute. Discard flow through. Spin at maximum speed for 1 minute to dry column.

Add 30 uL of Buffer EB directly to membrane. Wait 1 minute. Centrifuge at 10 000 g or less for 1 minute.

Fragmentation

Prepare fragmentation buffer:

| DNase I | 1 uL (Ambion) |
|---|---|
| 1X First strand buffer | 99 uL (Gibco-BRL) |

Add 1 uL of fragmentation buffer to each sample. Incubate at 37° C. for 15 minutes. Incubate at 95° C. for 5 minutes to heat-inactivate DNase.

Spin samples in speed vacuum to dry completely.

Hybridization

Resuspend the dried sample in the following hybridization mix:

| 50X dNTP | 1 uL |
|---|---|
| 20X SSC | 2.3 uL |
| sodium pyrophosphate 200 mM) | 7.5 uL |
| herring sperm DNA (1 mg/mL) | 1 uL |
| Vortex sample, centrifuge briefly, and add: | |
| 1% SDS | 3 uL |

Incubate at 95° C. for 2–3 minutes, cool at 20 room temperature for 20 minutes.

Hybridize samples to oligonucleotide arrays overnight. When oligonucleotides are 50 mers, hybridize samples at 65° C. When oligonucleotides are 30mers, hybridize samples at 57° C.

Washing after hybridization

| First wash: | Wash slides for 1 minute at 65° C. in Buffer 1 |
|---|---|
| Second wash: | Wash slides for 5 minutes at room temperature in Buffer 2 |
| Third wash: | Wash slides for 5 minutes at room temperature in Buffer 3 |

Buffer 1:

3× SSC, 0.03% SDS

Buffer 2:

1× SSC

Buffer 3:

0.2× SSC

After the three washes, dry the slides by centrifuging them, and then scan using appropriate laser power and photomultiplier tube gain.

Example 3

Expression of CGA7 and CJA8 in Colorectal Cancer Tissue Versus Normal Tissues

Expression studies were performed herein. CGA7 and CJA8 are up-regulated in colorectal cancer tissue. CGA7 and CJA8 are expressed in elevated amounts in colorectal cancer tissues, while both genes were found to be expressed in limited amounts or not at all in normal tissues, including adrenal gland, aorta, aortic valve, artery, bladder, bone marrow, brain, breast, CD14+ monocytes, CD14− cells, cervix, colon, diaphragm, esophagus, gallbladder, heart, kidney, liver, lungs, lymph node, muscle, vagus nerve, omentum, ovary, pancreas, prostate, salivary gland, skin, spinal cord, spleen, stomach, testis, thymus, thyroid, uterus, and vein/inferior vena cava as compared with colorectal cancer tissue. CGA7 is located on chromosome 2; CJA8 is located on chromosome 11.

Example 4

Expression Analysis

To identify genes that are up-regulated in colorectal cancer, oligonucleotide microarrays are interrogated with cRNAs derived from multiple tissues. More specifically, biotinylated-cRNAs are generated by in vitro transcription reactions (IVTs) from primary colorectal tumors and non-malignant samples made up of, for example, the following adult tissues and organs: adrenal gland, aorta, aortic valve, bladder, bone marrow, brain, breast, colonic epithelium, cervix, colon, diaphragm, esophagus, gallbladder, heart, ileum, jejunum, kidney, liver, lung, lymph node, muscle, pancreas, rectum, salivary gland, skin, small intestine, spinal cord, spleen, stomach, thymus, thyroid, trachea, ureter, uterus, vessel-artery. cRNA hybridization to the oligonucleotide microarrays is measured by average fluorescence intensity (AI), which is directly proportional to the expression level of the gene. To specifically calculate the overexpression of any gene in breast cancer, the following calculations are made:

1. The $15^{th}$ percentile value is subtracted from all samples to remove gene-specific background hybridization.
2. The lowest value is set at 10 units for the purpose of calculating cancer:normal tissue expression ratios.
3. The expression ratio of each gene is calculated to be the $90^{th}$ percentile of breast cancer expression divided by the $85^{th}$ percentile of normal adult tissue expression. The $90^{th}$ percentile is mathematically equal to the median of the top 20% of samples; likewise, the $85^{th}$ percentile corresponds to the median of the top 30%.
4. The genes are sorted by descending ratio.

Only genes with greater than or equal to 3-fold overexpression in breast cancer are selected as potential new therapeutic targets and/or diagnostic markers.

Examples 5

Antibodies

Antibodies to extracellular regions of encoded proteins are generated using several different approaches, including:
1. Using phage display to identify single-chain antibodies that recognize extracellular regions of a gene product.
2. Generating extracellular regions as secreted Fc fusion proteins, which are purified from extracellular media and then used as antigens in antibody production.
3. Synthesizing peptides from the extracellular region and using them as immunogen.
4. Generating heterologous cell lines that are transfected with cDNAs, or infected with retrovirus encoding cDNAs. These cell lines are then used in cellular immunizations.

We claim:

1. A method of detecting colorectal cancer comprising:
   a) determining the expression of a gene encoding CGA7 in a first colon tissue of a first individual; and
   b) comparing said expression of said gene with that of a normal colon tissue obtained from said first individual or a second unaffected individual; wherein a difference in said expression is an indication that the first individual may have colorectal cancer.

2. A method for determining the prognosis of an individual with colorectal cancer, comprising:
   a) determining the expression of a gene encoding CGA7 in colorectal cancer tissues in different states of the individual; and
   b) comparing the expression profile of the gene in the different states, wherein a higher level of the expression in a later state compared with an early state indicates a poor prognosis.

3. A method of detecting colorectal cancer comprising:
   a) determining the amount of mRNA encoding CJA8 or a fragment thereof in a first colon tissue of a first individual; and
   b) comparing said amount with that of a normal colon tissue obtained from said first individual or a second unaffected individual; wherein a difference in said expression is an indication that the first individual may have colorectal cancer.

4. A method for determining the prognosis of an individual with colorectal cancer, comprising:
   a) determining the expression of a gene encoding CJA8 in colorectal cancer tissues in different states of the individual; and
   b) comparing the expression profile of the gene in the different states, wherein a higher level of the expression in a later state compared with an early state indicates a poor prognosis.

* * * * *